United States Patent
Knox et al.

(10) Patent No.: US 9,144,491 B2
(45) Date of Patent: Sep. 29, 2015

(54) METHOD FOR MODIFYING THE REFRACTIVE INDEX OF AN OPTICAL MATERIAL

(75) Inventors: Wayne H. Knox, Pittsford, NY (US);
Dharmendra Jani, Fairport, NY (US);
Li Ding, San Jose, CA (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/238,143

(22) Filed: Sep. 21, 2011

(65) Prior Publication Data
US 2012/0310340 A1   Dec. 6, 2012

Related U.S. Application Data

(60) Provisional application No. 61/492,586, filed on Jun. 2, 2011.

(51) Int. Cl.
*B29D 11/00* (2006.01)
*A61F 2/16* (2006.01)
(Continued)

(52) U.S. Cl.
CPC ........... *A61F 2/1627* (2013.01); *A61F 9/00834* (2013.01); *A61L 27/16* (2013.01); *A61L 27/50* (2013.01); *A61L 27/52* (2013.01);
(Continued)

(58) Field of Classification Search
CPC ........... B29D 11/00355; A61F 2/1627; A61F 9/00834; A61L 27/16; A61L 27/50; A61L 27/52; A61L 2400/18; A61L 2430/16; G02C 2202/14; G02C 2202/12

USPC ............... 264/1.37, 1.7, 1.1, 400, 482
See application file for complete search history.

(56) References Cited

U.S. PATENT DOCUMENTS

| 3,959,281 A | 5/1976 | Beyerle et al. |
| 4,907,586 A | 3/1990 | Bille et al. |

(Continued)

FOREIGN PATENT DOCUMENTS

| EP | 0575885 A1 | 12/1993 |
| EP | 1234655 A1 | 8/2002 |

(Continued)

OTHER PUBLICATIONS

Chan et al., "Structural changes in fused silica after exposure to focused femtosecond laser pulses," Optics Letters, (vol. 26), (Issue. 21), (p. 1726-1728), (Nov. 1, 2001).

(Continued)

*Primary Examiner* — Mathieu Vargot
(74) *Attorney, Agent, or Firm* — Andrew J. Anderson, Esq.; Harter Secrest & Emery LLP

(57) ABSTRACT

A method for modifying the refractive index of an optical polymeric material. The method comprises continuously irradiating predetermined regions of an optical, polymeric material with femtosecond laser pulses to form a gradient index refractive structure within the material. An optical device includes an optical, polymeric lens material having an anterior surface and posterior surface and an optical axis intersecting the surfaces and at least one laser-modified, GRIN layer disposed between the anterior surface and the posterior surface and arranged along a first axis 45° to 90° to the optical axis, and further characterized by a variation in index of refraction across at least one of at least a portion of the adjacent segments and along each segment.

20 Claims, 29 Drawing Sheets

(51) Int. Cl.
*A61F 9/008* (2006.01)
*A61L 27/16* (2006.01)
*A61L 27/50* (2006.01)
*A61L 27/52* (2006.01)

(52) U.S. Cl.
CPC ......... *A61L 2400/18* (2013.01); *A61L 2430/16* (2013.01); *G02C 2202/12* (2013.01); *G02C 2202/14* (2013.01)

(56) References Cited

U.S. PATENT DOCUMENTS

| | | | |
|---|---|---|---|
| 5,220,359 A | 6/1993 | Roffman | |
| 5,849,006 A | 12/1998 | Frey et al. | |
| 5,964,748 A | 10/1999 | Peyman | |
| 6,197,057 B1 | 3/2001 | Peyman et al. | |
| 6,261,220 B1 | 7/2001 | Frey et al. | |
| 6,270,221 B1 | 8/2001 | Liang et al. | |
| 6,271,914 B1 | 8/2001 | Frey et al. | |
| 6,450,642 B1 | 9/2002 | Jethmalani et al. | |
| 6,489,589 B1 | 12/2002 | Alexander | |
| 6,770,728 B2 | 8/2004 | Watanabe et al. | |
| 6,849,671 B2 | 2/2005 | Steffen et al. | |
| 6,857,744 B2 | 2/2005 | Nakada et al. | |
| 6,887,269 B1 | 5/2005 | Hampp et al. | |
| 7,037,954 B2 | 5/2006 | Baba et al. | |
| 7,085,469 B2 | 8/2006 | Mune et al. | |
| 7,105,110 B2 | 9/2006 | Platt et al. | |
| 7,789,910 B2 | 9/2010 | Knox et al. | |
| 2002/0048726 A1 | 4/2002 | Kikkawa et al. | |
| 2002/0100990 A1 | 8/2002 | Platt et al. | |
| 2003/0049850 A1 | 3/2003 | Golden | |
| 2003/0052311 A1 | 3/2003 | Inagaki et al. | |
| 2004/0015236 A1 | 1/2004 | Sarfarazi | |
| 2004/0206940 A1 | 10/2004 | Boschetti et al. | |
| 2004/0238977 A1 | 12/2004 | Ilyashenko | |
| 2004/0243111 A1 | 12/2004 | Bendett et al. | |
| 2004/0265737 A1 | 12/2004 | Hanamura et al. | |
| 2005/0018130 A1 | 1/2005 | Dahi et al. | |
| 2005/0027031 A1 | 2/2005 | Chang et al. | |
| 2005/0116207 A1 | 6/2005 | Tani | |
| 2005/0187622 A1 | 8/2005 | Sandstedt et al. | |
| 2005/0192563 A1 | 9/2005 | Platt et al. | |
| 2005/0195361 A1 | 9/2005 | Jethmalani et al. | |
| 2006/0017990 A1 | 1/2006 | Platt et al. | |
| 2006/0083890 A1 | 4/2006 | Takizawa | |
| 2006/0106126 A1 | 5/2006 | Chang et al. | |
| 2006/0135952 A1 | 6/2006 | Curatu et al. | |
| 2007/0004863 A1 | 1/2007 | Mentak | |
| 2007/0087284 A1* | 4/2007 | Fleming et al. | 430/269 |
| 2007/0172905 A1 | 7/2007 | Taran et al. | |
| 2007/0173794 A1 | 7/2007 | Frey et al. | |
| 2008/0001320 A1 | 1/2008 | Knox et al. | |
| 2009/0143858 A1 | 6/2009 | Knox et al. | |
| 2009/0157178 A1 | 6/2009 | Hampp | |
| 2009/0218519 A1* | 9/2009 | McLeod | 250/492.1 |
| 2009/0287306 A1 | 11/2009 | Smith et al. | |
| 2010/0228345 A1* | 9/2010 | Bille | 623/6.23 |

FOREIGN PATENT DOCUMENTS

| | | |
|---|---|---|
| EP | 1703313 A1 | 9/2006 |
| EP | 1882463 A1 | 1/2008 |
| JP | 9-178901 A | 7/1997 |
| JP | 2001147301 | 5/2001 |
| JP | 2007501794 | 2/2007 |
| WO | 9210980 A1 | 7/1992 |
| WO | WO 00/41650 A1 | 7/2000 |
| WO | WO 01/71411 A2 | 9/2001 |
| WO | WO 2004/006794 A1 | 1/2004 |
| WO | WO 2005/015268 A2 | 2/2005 |
| WO | WO 2006/002201 A2 | 1/2006 |
| WO | WO 2006/112952 A2 | 10/2006 |
| WO | 2007137102 A2 | 11/2007 |
| WO | WO 2008/002795 A2 | 1/2008 |
| WO | 2009143054 A2 | 11/2009 |

OTHER PUBLICATIONS

Ding et al., "Large refractive index change in silicone-based and non-silicone-based hydrogel polymers induced by femtosecond laser micro-machining," Opt Soc of America, (vol. 14), (Issue. 24), (p. 11901-11909), (Nov. 27, 2006).

Ding et al., "Micro-Raman spectroscopy of refractive index microstructures in silicone-based hydrogel polymers created by high-repetition-rate femtosecond laser micromachining," Opt Soc of America, Apr. 2009, (vol. 26), (Issue. 4), (p. 595-602).

Eaton et al., "Heat accummulation effects in femtosecond laser-written waveguides with variable repetition rate," Opt Soc of America, (vol. 13), (Issue. 12), (p. 4708-4716), (Jun. 13, 2005).

Menon et al., "Zone-Plate-Array lithography (ZPAL): optical maskless lithography for cost-effective patterning," Proc SP1E, May 2005, (p. 330-339).

Menon et al., "Maskless lithography," Materialstoday, Feb. 2005, (p. 26-33).

Oshika et al., "Three year prospective, randomized evaluation of intraocular lens implantation through 3.2 and 5.5 mm incisions," J Cat & Refr Surg, Apr. 1998, (vol. 24), (p. 509-514).

Trager et al., "Polymers for in vivo tuning of refractive properties in intraocular lenses," Macromol Biosci, 2008, (vol. 8), (Issue. 2), (p. 177-183).

\* cited by examiner

METHOD FOR MODIFYING THE REFRACTIVE INDEX OF AN OPTICAL MATERIAL

CROSS REFERENCE

This application claims the benefit under 35 USC 119(e) of Provisional Patent Application No. 61/492,586 filed Jun. 2, 2011 which is incorporated by reference herein.

CREATE ACT STATEMENT

The claimed invention was made by, on behalf of, or in connection with one or more of the following parties to a joint university-corporation research agreement: The University of Rochester, and Bausch & Lomb, Inc. The agreement was in effect on and before the date the claimed invention was made, and the claimed invention was made as a result of activities undertaken within the scope of the agreement.

FIELD OF THE INVENTION

Embodiments of the invention are directed to a method for using a laser to modify the refractive properties of optical components or devices such as, but not limited to, intraocular lenses (IOLs), contact lenses, corneal inlays, and other such optical components or devices that include hydrogel or hydrophobic acrylate materials, the resulting optical components or devices, and other applications.

DESCRIPTION OF RELATED ART

In general, there are two types of intraocular lenses, referred to as pseudo-phakic IOLs and phakic IOLs. The former type replaces the eye's natural, crystalline lens, usually to replace a cataractous lens that has been removed. The latter type is used to supplement an existing lens and functions as a permanent corrective lens, which is implanted in the anterior or posterior chamber to correct refractive errors of the eye. The power of the lens (i.e., point focus on the retina from light originating at infinity) to be implanted is determined based on pre-operative measurements of ocular length and corneal curvature of each patient. The pre-operative measurements are conducted with the hope that the patient will need little, if any, vision correction following the surgery. Unfortunately, due to errors in measurement, variable lens positioning, or wound healing, most patients undergoing surgery will not enjoy optimal vision without some form of vision correction following the surgery. Since the power of a typical (non-accommodating) IOL is fixed and cannot be adjusted post-implantation (in-situ), most patients must use corrective lenses such as eye glasses or contact lenses following cataract surgery to optimize their vision.

One potential alternative to post-operative, corrective lenses is a light-adjustable intraocular lens whose refractive properties can be modified following insertion of the lens into a human eye. Such a lens is reported in U.S. Pat. No. 6,450,642, hereafter referred to as the Calhoun Patent. The light-adjustable lens is said to comprise (i) a first polymer matrix and (ii) a refraction modulating composition (RMC) that is capable of stimulus-induced polymerization. As stated, when a portion of the described lens is exposed to light of sufficient intensity, the RMC forms a second polymer matrix. The process is said to result in a light adjusted, power-modified lens.

As described in the Calhoun Patent, the first polymer matrix and the RMC are selected such that the components that comprise the RMC are capable of diffusion within the first polymer matrix. Put another way, a loose first polymer matrix will tend to be paired with larger RMC components and a tight first polymer matrix will tend to be paired with smaller RMC components. Upon exposure to an appropriate energy source (e.g., heat or light), the RMC typically forms a second polymer matrix in the exposed region of the optical element. After exposure, the RMC in the unexposed region will migrate into the exposed region over time. The amount of RMC migration into the exposed region is said to be time dependent and controllable. If enough time is permitted, the RMC components will re-equilibrate and redistribute throughout the lens material (i.e., the first polymer matrix, including the exposed region). When the region is re-exposed to the energy source, the RMC that has since migrated into the region polymerizes to further increase the formation of the second polymer matrix. This process (exposure followed by an appropriate time interval to allow for diffusion) may be repeated until the exposed region of the optical element has reached the desired property (e.g., power, refractive index, or shape). The entire optical element is then exposed to an energy source to "lock-in" the desired lens property by polymerizing the remaining RMC in the lens material. Overall, the power of the lens is changed by a shape change caused by the migration of the RMC and subsequent polymerization(s).

U.S. Pat. No. 7,105,110 describes a method and instrument to irradiate a light adjustable lens as described in the Calhoun Patent with an appropriate amount of radiation in an appropriate pattern. The method is said to include aligning a source of the modifying radiation so as to impinge the radiation onto the lens in a pattern, and controlling the quantity of the impinging radiation. The quantity of the impinging radiation is controlled by controlling the intensity and duration of the irradiation.

Applicants have previously described methods for modifying the refractive index of optical polymeric materials using very short pulses from a visible or near-IR laser having a pulse energy from 0.5 nJ to 1000 nJ. See, U.S. Publication No. 2008/0001320. The intensity of light is sufficient to change the refractive index of the material within the focal volume, whereas portions just outside the focal volume are minimally affected by the laser light. Irradiation within the focal volume results in refractive optical structures characterized by a positive change in refractive index of 0.005 or more relative to the index of refraction of the bulk (non-irradiated) polymeric material. Under certain irradiation conditions and in certain optical materials, a change in refractive index of 0.06 was measured. The irradiated regions of the optical material can take the form of two- or three-dimensional, area or volume filled refractive structures. The refractive structures are formed by scanning the laser over a select region of the polymeric material resulting in refractive optical structures that can provide spherical, aspherical, toroidal, or cylindrical correction to a lens. In fact, any optical structure can be formed to yield positive or negative power corrections to the lens. Moreover, the optical structures can be stacked vertically or written in separate planes in the polymeric material to act as a single lens element. In U.S. Pat. No. 7,789,910 Applicants describe using Raman spectroscopy as an investigative approach to determine what, if any, structural, chemical or molecular change is occurring within the focal volume of the optical polymeric materials that might explain the observed change in the index of refraction.

In U.S. Publication No. 2009/0287306, Applicants describe a similar process to provide dioptic power changes in optical polymeric materials that contain a photosensitizer. The photosensitizer is present in the polymeric material to enhance the photoefficiency of the two-photon process used to form the refractive structures. In some instances, the rate at which the laser light is scanned across the polymeric material can be increased 100-fold with the inclusion of a photosensitizer and still provide a similar change in the refractive index of the material.

U.S. Publication No. 2009/0157178 is said to describe a polymeric intraocular lens material that can provide a photo-induced, chemical change in the material resulting in a change in focal length (power) or the aspheric character of the lens by modifying the index of refraction of the material with laser light. The photoinduced chemistry in the material is said to occur by exposure of the material to laser light over a broad spectral range of 200 nm to 1500 nm. In the case of UV light from 200 nm to 400 nm the photoinduced chemistry is said to be a single-photon process, whereas a two-photon process is envisioned with light from 400 to 1500 nm. Only photoinduced chemistry using a laser pulse of 313 nm and a total irradiation dose ranging from 0.05 $J/cm^2$ to 2 $J/cm^2$ is described, which is not surprising to Applicants. Early on, Applicants had investigated a similar bond-breaking/bond formation approach in the hopes of inducing optical changes in polymeric materials. Applicants learned that light in the UV was necessary, and a photo-efficient, two-photon process remained elusive for inducing such chemical or structural changes as well observed changes in the index of refraction of the material.

U.S. Publication No. 2010/0228345 is said to describe a lens such as an intraocular lens in which the refractive index within the laser focus (loci) are modified to a depth of 5 μm to 50 μm. The method is said to provide dioptic power changes to the lens by a change in refractive index ($\Delta n$) of the lens material at different locus positions, e.g., between a lowest value of $\Delta n=0.001$ to a highest value of $\Delta n=0.01$, exploiting a modulo $2\pi$ phase wrapping technique. The described irradiation method uses bursts of femtosecond (fs) laser pulses to change the refractive index of the irradiated material through a multiphoton absorption mechanism. However, to achieve the desired dioptic changes the resulting modified index optical layers in the material must be at least 50 microns (μm) thick.

There is an ongoing need for new and improved techniques and materials, and vision components resulting therefrom, for improving human vision. Such components may include IOLs for use following cataract surgery, or may be in the form of corneal inlays or other implantable vision correction devices. There are also advantages and benefits that would result from such techniques and components allowing in-situ modification of refractive properties (e.g., refractive index, dioptric power).

SUMMARY

An embodiment of the invention is directed to a method for providing changes in refractive power of an optical device. The method includes a step of providing an optical device with an optical, polymeric lens material having an anterior surface and posterior surface and an optical axis intersecting the surfaces. The method also includes the step of forming at least one laser-modified, gradient index (GRIN) layer disposed between the anterior surface and the posterior surface with light pulses from a visible or near-IR laser and scanning the pulses along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned. In various non-limiting aspects:

- the at least one laser-modified, GRIN layer is arranged along a first axis and is tilted from between about 45° to 135° to the optical axis;
- the polymeric lens material includes a photosensitizer;
- the photosensitizer includes at least one two-photon absorption chromophore having a two-photon cross-section of at least 10 GM between 750 nm and 1100 nm;
- the photosensitizer is part of a polymerizable monomer or is physically dispersed within the optical polymer;
- forming the at least one laser-modified, gradient index GRIN layer includes irradiating select regions of the optical, polymeric lens material with a continuous stream of laser pulses having a pulse energy from 0.01 nJ to 20 nJ;
- focusing a plurality of very short laser pulses having a defined focal volume, with a spectral wavelength of between about 650 nanometers (nm) to about 950 nm, into the material. The laser pulses have a repetition rate from 10 MHz to 300 MHz, a pulse duration of 10 fs to 500 fs, an average power from 20 mW to 260 mW, and a pulse energy from 0.01 nJ to 20 nJ;
- the optical device is an intraocular lens whose refractive properties are modified prior to the surgical insertion of the lens in a human eye. In this aspect, the irradiation process may be performed in a manufacturing environment. The refractive properties may be designed to enhance the depth of field of the lens or create select regions of variable power to custom fit the lens to the vision correction needs of a patient. Alternatively, the refractive properties may be designed to create a multi-focal lens;
- the optical device is an intraocular lens, or corneal inlay, and the forming of the at least one laser-modified GRIN layer is performed following the surgical placement of the optical device in an eye of a patient, by e.g., an ophthalmic practitioner;
- the plurality of adjacent refractive segments of the GRIN layer has an independent line width of one to five μm and the intersegment spacing of two adjacent refractive segments is less than an average linewidth of the two adjacent segments;
- the plurality of adjacent refractive segments are line segments;
- the plurality of adjacent refractive segments are concentric segments outwardly projected from a central point along a first axis;
- the plurality of adjacent refractive segments are arcuate or curved segments;
- the plurality of segments of the GRIN layer are characterized by a constant positive change in the index of refraction of at least one of: —(i) a portion of refractive segments in the direction scanned; and (ii) along a portion of an axis that is transverse to the refractive segments, in relation to the index of refraction of the lens material;
- the plurality of segments of the GRIN layer are characterized by a constant rate of increasing or decreasing positive change in the index of refraction of at least one of: (i) a portion of refractive segments in the direction scanned; and (ii) along a portion of an axis that is transverse to the refractive segments, in relation to the index of refraction of the lens material;
- the at least one laser-modified, GRIN layer has a quadratic profile;
- the at least one laser-modified, GRIN layer exhibits little or no scattering loss, i.e., the formed GRIN layer is not clearly visible under appropriate magnification without phase-contrast enhancement such that the GRIN layer is virtually transparent to the human eye without some form of image enhancement;

forming the at least one laser-modified, GRIN layer includes forming from two to ten laser-modified, GRIN layers;

forming the at least one laser-modified, GRIN layer includes forming from two to ten laser-modified, GRIN layers arranged either above or below the at least one laser-modified, GRIN layer along a second axis substantially perpendicular to the first axis;

the GRIN layer has an independent thickness of from 2 μm to 10 μm, and the GRIN layers exhibit little or no scattering loss;

the two to ten GRIN layers have an interlayer spacing of non-modified polymeric lens material having a thickness of from 5 μm to 10 μm.

An embodiment of the invention is directed to an optical device having a gradient index structure. The device includes an optical, polymeric lens material having an anterior surface and posterior surface and an optical axis intersecting the surfaces. The device also includes at least one laser-modified, GRIN layer disposed between the anterior surface and the posterior surface and arranged along a first axis arranged 45° to 135° to the optical axis. The at least one laser-modified GRIN layer comprises a plurality of adjacent refractive segments, and is characterized by a variation in index of refraction of at least one of: (i) a transverse cross section of the adjacent refractive segments; and (ii) a lateral cross section of refractive segments. In various non-limiting aspects:

the plurality of adjacent refractive segments are line segments;

the plurality of adjacent refractive segments are selected from the group consisting of concentric and arcuate or curved segments;

the polymeric lens material includes a photosensitizer;

the photosensitizer includes a chromophore with a two-photon, absorption cross section of at least 10 GM between 750 nm and 1100 nm;

the plurality of adjacent refractive segments of the GRIN layer have an independent line width of one to five μm and an intersegment spacing of two adjacent segments is less than an average line width of the two adjacent segments;

the plurality of refractive segments of the GRIN layer are characterized by a constant positive change in the index of refraction along at least one of the first axis and a transverse second axis, the change in the index of refraction in relation to non-modified polymeric lens material;

the plurality of refractive segments of the GRIN layer are characterized by a constant or variable rate of increasing or decreasing positive change in the index of refraction along at least one of the first axis and a transverse second axis, the change in the refractive index in relation to non-modified polymeric lens material;

the polymeric lens material is a hydrogel;

the device is an intraocular lens or a corneal inlay.

These and other features, attributes, and characteristics of the embodied invention will now be described in detail with reference to the appended drawing figures.

BRIEF DESCRIPTION OF THE DRAWINGS

The embodied invention will be better understood from the following description and in consideration with the accompanying figures. It is to be expressly understood, however, that each of the figures are provided to merely illustrate and describe the embodiments of the invention and are not intended to further limit the claimed embodiments of the invention.

FIG. 26 B is graphical representation of another gradient index profile of a GRIN layer along an axis transverse to the scan direction;

FIG. 26 C is a graphical representation of another gradient index profile of a GRIN layer along an axis transverse to the scan direction;

DETAILED DESCRIPTION OF EXEMPLARY EMBODIMENTS OF THE INVENTION

Figure 1A:
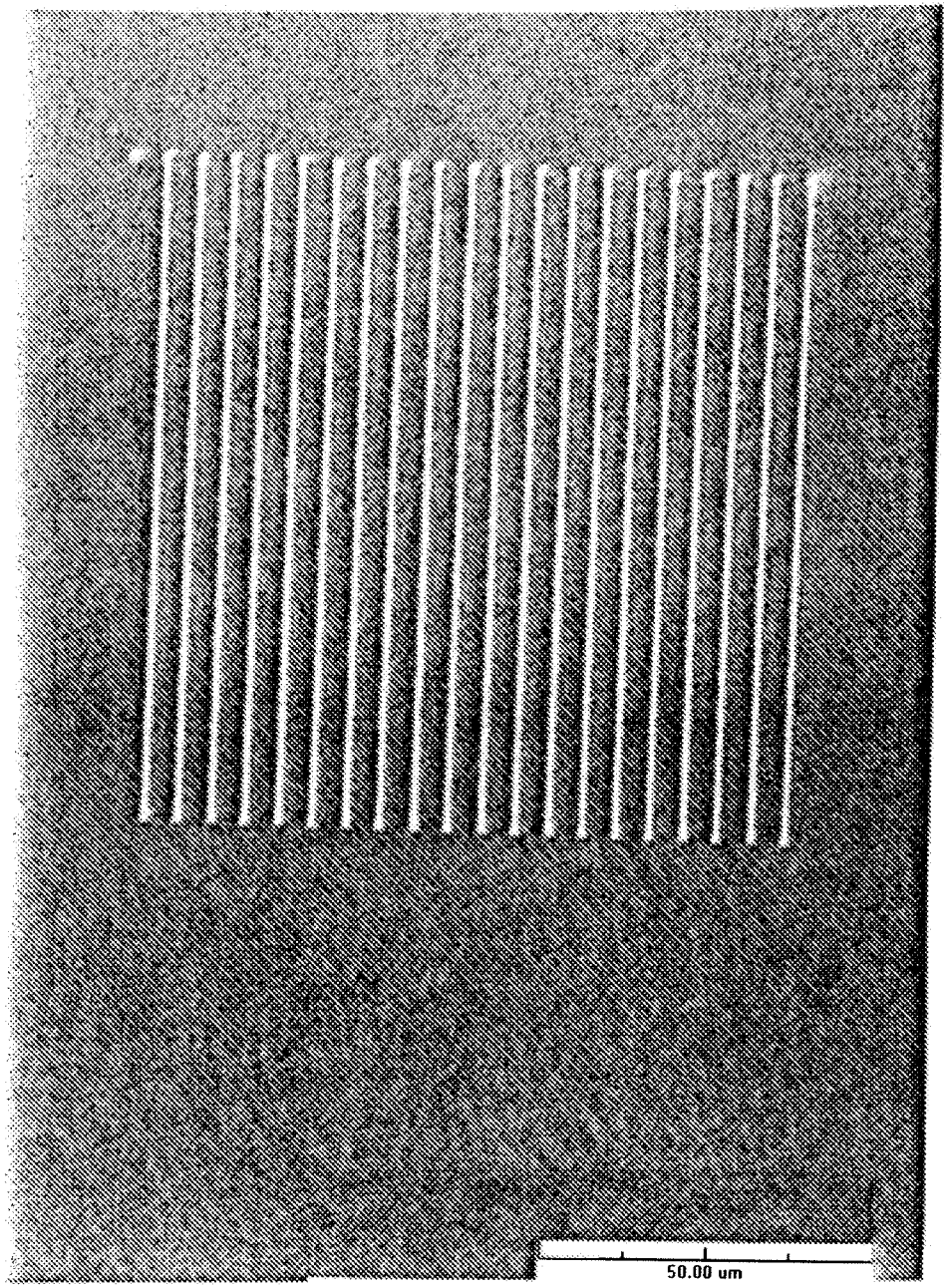
FIG. 1A is a microscope photograph of a line grating written in an optical, polymeric material produced by laser irradiation.

If very short laser pulses of sufficient energy are used to irradiate an optical, polymeric material, the intensity of light within the focal volume will cause a nonlinear absorption of photons (typically multi-photon absorption) and lead to a change in the refractive index of the material within the focal volume. Moreover, the material just outside of the focal volume will be minimally affected by the laser light. The femtosecond laser pulse sequence pertaining to an illustrative embodied invention operates at a high repetition-rate, e.g., 80 MHz, and consequently the thermal diffusion time (>0.1 μs) is much longer than the time interval between adjacent laser pulses (~11 ns). Under such conditions, absorbed laser energy can accumulate within the focal volume and increase the local temperature. This thermal mechanism likely plays a role in the formation of laser-induced refractive structures in optical, polymeric materials. Moreover, the presence of water in the polymeric material is believed to advantageously influence the formation of the refractive structures. As such, optical hydrogel polymers provide much greater processing flexibility in the formation of the refractive structures as compared to zero or low water content optical polymers, e.g., the hydrophobic acrylates or low-water (1% to 5% water content) acrylate materials.

The method comprises irradiating select regions of an optical polymeric material such as, e.g., an optical hydrogel material, with a laser. The irradiated regions exhibit little or no scattering loss, which means that the resulting refractive structures that form in the focal volume are not clearly visible under appropriate magnification without phase contrast enhancement. In other words, the refractive structures are virtually transparent to the human eye without some form of image enhancement. An optical material is a polymeric material that permits the transmissions of at least 80% of visible light through the material, that is, an optical material does not appreciably scatter or block visible light.

An exemplary method may be more advantageously carried out if an optical polymeric material, such as, e.g., an optical hydrogel material, includes a photosensitizer. The presence of the photosensitizer permits one to set a scan rate to a value that is at least fifty times greater, or at least 100 times greater, than a scan rate without a photosensitizer present in the material, and yet provide similar refractive structures in terms of the observed change in refractive index of the material in the focal volume. Alternatively, the photosensitizer in the polymeric material permits one to set an average laser power to a value that is at least two times less, more particularly up to four times less, than an average laser power without a photosensitizer in the material, yet provide similar refractive structures. We believe that a photosensitizer having a chromophore with a relatively large multi-photon absorption cross section captures the light radiation (photons) with greater efficiency and then transfers that energy to the optical polymeric material within the focal volume. The transferred energy leads to the formation of the refractive structures and the observed change in the refractive index of the material in the focal volume.

In addition, Applicants previously investigated whether the formed refractive structures resulting from the described two-photon process led to significant chemical changes, in terms of the breaking or forming of chemical bonds, in the hydrogel polymeric materials, See, U.S. Pat. No. 7,789,910, the disclosure of which is incorporated herein by reference. Applicants were quite surprised to find little or no difference in the Raman spectrum between regions of the polymeric materials that were exposed to the laser pulses and those regions that were not exposed. Typically, Raman spectroscopy is used to provide information on the structural or molecular changes that occur in materials. In the Raman scattering experiments, the hydrogel polymer samples were placed in a confocal micro-Raman spectrometer equipped with an X-Y scan stage with nanometer resolution. A 632.8 nm He—Ne laser was focused on the surface of the material in order to obtain the Raman scattering signal. Due to the difference between the refractive indices of the bulk and the irradiated regions, the scattered light at the interface was monitored in order to ensure the laser focus was located in the irradiated region. A comparison of the two spectra strongly suggests that there is no significant structural or chemical change between the irradiated regions and the base material.

The above Raman results were surprising in light of recent Raman spectra analysis of fused silica modified by femtosecond laser pulses. See, J. W. Chan, T. Huser, S. Risbud, D. M. Krol, in "*Structural changes in fused silica after exposure to focused femtosecond laser pulses*," Opt. Lett. 26, 1726-1728 (2001). The results of Applicants Raman experiments, however, may explain why one does not observe any light scattering by the irradiated regions (refractive structures) in the polymeric hydrogel materials. The Raman spectra also suggest that low pulse energy, femtosecond irradiation of optical, hydrogel materials do not cause strong structural changes in the materials even when the change of the refractive index is much higher than that obtained for fused silica.

To date, we have used a 60×0.70NA Olympus LUCPlan-FLN long-working-distance microscope objective with variable spherical aberration compensation. As indicated by the following equation $$\Delta T(r, z, t=0) = \frac{\beta \tau_P [I(0, 0)]^2 \exp\left[-4\left(\frac{r^2}{a^2} + \frac{z^2}{b^2}\right)\right]}{c_p \rho}$$

the localized instantaneous temperature depends on both the pulse intensity and the magnitude of the two-photon absorption (TPA) coefficient. In order to produce an optical modification of a material that is of purely refractive character, i.e., non-absorbing or scattering, it is important to avoid optical damage, i.e., observed burning (scorching) or carbonization of the polymeric material. Such material or optical damage can be caused by excitation intensities exceeding a critical free-electron density. For hydrogel polymers containing a fair amount of water, the optical breakdown threshold is much lower than that in silica glasses. This breakdown threshold limits the pulse energy (in many cases to approximately 0.1 nJ to 20 nJ) that the hydrogel polymers can tolerate, and yet provide the observed changes in the refractive index within the focal volume.

The irradiation process and conditions described herein are very different from what has been reported in femtosecond laser micromachining studies in silica, in which much larger pulse energies and a much larger temperature increase (several thousand Kelvin) have been observed. See, S. M. Eaton et al. in "*Heat accumulation effects in femtosecond laser-written waveguides with variable repetition rate*," Opt. Express 2005, 13, 4708-16. Also, the specific heat constant $C_p$ of water is much larger than that of silica glass ($C_p$=840 $JK^{-1}$ $kg^{-1}$) and, therefore, the presence of water in the hydrogel polymeric material is believed to moderate the temperature increase in the focal volume.

Another way to increase energy absorption at a given intensity level is to increase the nonlinear absorption coefficient $\beta$ by doping the optical, polymeric material with a particular chromophore and tuning the short pulse laser near a two-photon transition of the chromophore. In this regard, we have prepared optical, hydrogel materials doped with a non-polymerizable photosensitizer or a polymerizable photosensitizer. The photosensitizer will include a chromophore having a two-photon, absorption cross-section of at least 10 GM between a laser wavelength range of 750 nm to 1100 nm. In the former case of a non-polymerizable photosensitizer, we prepared solutions containing a photosensitizer and allowed the optical, hydrogel polymeric materials to come in contact with such solutions to allow up-take of the photosensitizer into the polymeric matrix of the polymer. In the later case of a polymerizable photosensitizer, we used monomers containing a chromophore, e.g., a fluorescein-based monomer, in the monomer mixture such that the chromophore becomes part of the polymeric matrix.

One of ordinary skill would recognize that one could easily use a solution containing a non-polymerizable photosensitizer to dope an optical, polymeric material that had been prepared with a polymerizable photosensitizer. Also, it is to be understood that the chromophoric entities could be the same or different in each respective phoosensitizer.

Our studies have shown that by doping the hydrogel material with the photosensitizer either by solution doping or by using a polymerizable photosensitizer, the localized temperature increase can reach a transition point of the polymer; the goal being to reach this transition point to provide a desired change in the refraction index, yet maintain a safe margin of intensity below the damage threshold level of the hydrogel material.

It is also important to note that the photosensitizer relied upon by Applicants to increase the photoefficiency of the two-photon process, and thereby, increase the photoefficiency of making the refractive structures resulting in the observed change in the refractive index of the polymeric hydrogel materials, does not undergo significant structural or chemical transformation in the process. Again, no changes in the Raman spectra of photosentized polymeric materials is observed between the irradiated and non-irradiated regions. This is consistent with the order of magnitude(s) increase in the observed efficiency for forming the refractive structures with material doped with a photosensitizer. For example, Applicants have observed an increase in the efficiency of forming the refractive structures by 100-fold or more simply by doping a given hydrogel material with 0.17 wt. % of a polymerizable monomer having a chromophore necessary for photosensitization. This very small concentration of doped photosensitizer cannot by itself account for the observed increase in efficiency.

The concentration of a polymerizable, monomeric photosensitizer having a two-photon, chromophore in an optical material, preferably an optical, hydrogel material, can be as low as 0.05 wt. % and as high as 10 wt. %. Exemplary concentration ranges of polymerizable monomer having a two-photon, chromophore in an optical, hydrogel material is from 0.1 wt. % to 6 wt. %, 0.1 wt. % to 4 wt. %, and 0.2 wt. % to 3 wt. %. In various aspects, the concentration range of polymerizable monomer photosensitizer having a two-photon, chromophore in an optical, hydrogel material is from 0.4 wt. % to 2.5 wt. %.

Due to the high repetition rate pulse sequence used in the irradiation process, the accumulated focal temperature increase can be much larger than the temperature increase induced by a single laser pulse. The accumulated temperature increases until the absorbed power and the dissipated power are in dynamic balance. For hydrogel polymers, thermal-induced additional crosslinking within the polymer network can produce a change in the refractive index as the local temperature exceeds a transition temperature. If the temperature increase exceeds a second threshold, a somewhat higher temperature than the transition temperature, the polymer is pyrolytically degraded and carbonized residue and water bubbles are observed. In other words, the material exhibits visible optical damage (scorching). As a result of our investigations described herein, each of the following experimental parameters such as laser repetition rate, laser wavelength and pulse energy, TPA coefficient, and water concentration of the materials should be considered so that a desired change in the refractive index can be induced in the hydrogel polymers without optical damage.

The pulse energy and the average power of the laser, and the rate at which the irradiated regions are scanned, will in-part depend on the type of polymeric material that is being irradiated, how much of a change in refractive index is desired and the type of refractive structures one wants to create within the material. The selected pulse energy will also depend upon the scan rate and the average power of the laser at which the refractive structures are written into the polymer material. Typically, greater pulse energies will be needed for greater scan rates and lower laser power. For example, some materials will call for a pulse energy from 0.05 nJ to 100 nJ or from 0.2 nJ to 10 nJ.

Within the stated pulse energies above, the optical, hydrogel polymeric material is irradiated at a scan rate of at least 0.1 mm/s, from 0.1 mm/s to 10 mm/s or from 0.4 mm/s to 4 mm/s.

Within the stated pulse energies and scan rates above, the average laser power used in the irradiation process is from 10 mW to 400 mW, or from 40 mW to 220 mW.

In one aspect, the average pulse energy is from 0.2 nJ to 10 nJ and the average laser power is from 40 mW to 220 mW. The laser also operates within a wavelength of 650 nm to 950 nm. Within the stated laser operating powers, the optical, hydrogel polymeric material is irradiated at a scan rate from 0.4 mm/s to 4 mm/s.

A photosensitizer will include a chromophore in which there is little or no intrinsic linear absorption in the spectral range of 600-1000 nm. The photosensitizer is present in the optical, hydrogel polymeric material to enhance the photoefficency of the two-photon absorption required for the formation of the described refractive structures. Photosensitizers of particular interest include, but are not limited to, the following compounds. The compounds below are merely exemplary.

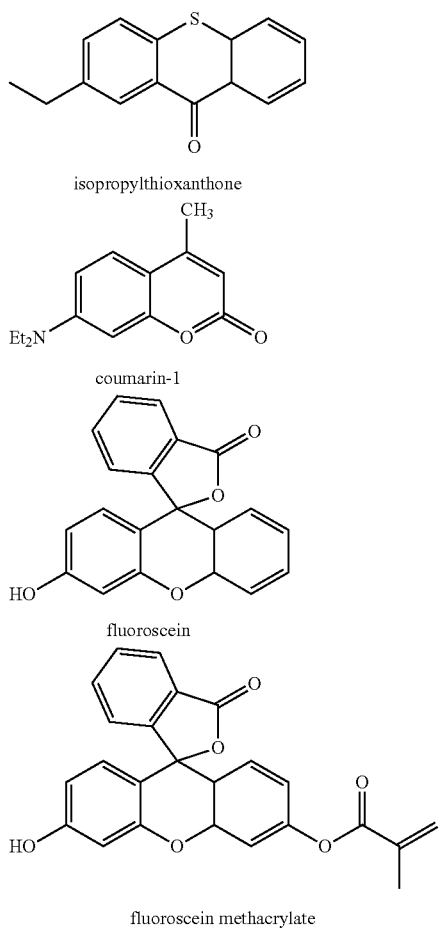

isopropylthioxanthone coumarin-1 fluoroscein fluoroscein methacrylate

As is described in greater detail in the Example section, a commercial IOL material, Akreos®, presently marketed by Bausch & Lomb, was subjected to laser irradiation according to the processes described herein. An Akreos® IOL is a HEMA-based, hydrogel material with 26% to 28% water content. The micromachining process was used to imprint refractive structures in an Akreos® IOL without photosensitizer and an Akreos® IOL doped with a solution containing 17 wt. % cormarin-1. The irradiation experiments were conducted with both dry and hydrated materials. The refractive structures formed only in the hydrated materials.

In brief, the magnitude of the measured change in refractive index was at least ten times greater in the Akreos® IOL doped with the coumarin solution at a given scan rate and an average laser power than the Akreos® IOL without the coumarin. Surprisingly, an increase in scan rate to 1 mm/s at an average laser power of 160 mW provided refractive structures with a change in refractive index of 0.02 to 0.03. Moreover, reducing the laser power to 60 mW still provided refractive structures with a change in refractive index of about 0.005.

In another illustrative aspect, a balafilcon A silicone hydrogel was prepared by adding fluorescein monomer (0.17% by weight) as a polymerizable photosensitizer to the polymer monomer mixture. The balafilcon A doped with fluorescein was then subjected to laser radiation according to the processes described herein. Again, the described irradiation process was used to imprint refractive structures in the silicone hydrogel without photosensitizer and the silicone hydrogel doped with 0.17 wt. % fluorescein monomer. Again, experiments were conducted with both dry and hydrated materials, and again, the refractive structures formed only in the hydrated materials. In brief, the magnitude of the measured change in refractive index was at least ten times greater in the balafilcon A silicone hydrogel doped with 0.17 wt. % fluorescein monomer at an average laser power of 60 mW than balafilcon A without the photosensitizer. This 10-fold difference in change in refractive index was observed even with a 10-fold increase in scan rate in the photosensitized material; i.e., 0.5 mm/s in the undoped material and 5.0 mm/s in the photosensitized material.

In some cases, the formation of refractive structures as described requires that the pulse width be preserved so that the pulse peak power is strong enough to exceed the nonlinear absorption threshold of the optical polymeric material. However, the glass of the focusing objective(s) significantly increases the pulse width due to the positive dispersion of the glass. A compensation scheme is used to provide a corresponding negative dispersion that can compensate for the positive dispersion introduced by the focusing objective(s). Accordingly, a compensation scheme can be used to correct for the positive dispersion introduced by the focusing objective(s). The compensation scheme can include an optical arrangement selected from the group consisting of at least two prisms and at least one mirror, at least two diffraction gratings, a chirped mirror and dispersion compensating mirrors to compensate for the positive dispersion introduced by the focus objective.

In different aspects, the compensation scheme included at least one prism, in many cases at least two prisms, and at least one mirror to compensate for the positive dispersion of the focusing objective. In another aspect, the compensation scheme included at least two gratings to compensate for the positive dispersion of the focusing objective. Any appropriate combination of prisms, gratings and/or mirrors can be used for the compensation scheme.

The laser will generate light with a wavelength in the range from violet to near-infrared. In various aspects, the wavelength of the laser is in the range from 400 nm to 1500 nm, from 400 nm to 1200 nm, or from 650 nm to 950 nm.

In an exemplary aspect, the laser is a pumped Ti:sapphire laser with an average power of 10 mW to 1000 mW. Such a laser system will generate light with a wavelength of approximately 800 nm. In another exemplary aspect, an amplified fiber laser that can generate light with a wavelength from 1000 nm to 1600 nm may be used.

The laser will have a peak intensity at focus of greater than $10^{13}$ W/cm$^2$. At times, it may be advantageous to provide a laser with a peak intensity at focus of greater than $10^{14}$ W/cm$^2$, or greater than $10^{15}$ W/cm$^2$.

The ability to form refractive structures in optical polymeric materials provides an important opportunity to an ophthalmic surgeon or practitioner to modify the refractive index of an optical device, e.g., an intraocular lens or corneal inlay, following implantation of the device into an eye of a patient. The method allows the surgeon to correct aberrations as a result of the surgery. The method also allows the surgeon to adjust the refractive properties of the lens or inlay by adjusting the refractive index in the irradiated regions based on the vision correction required of each patient. For example, starting from a lens of selected power (will vary according to the ocular requirements of the patient), the surgeon can further adjust the refractive properties of the lens to correct a patient's vision based upon the individual needs of the patient. In essence, an intraocular lens would essentially function like a contact lens or glasses to individually correct for the refractive error of a patient's eye. Moreover, because the implanted lens can be adjusted by adjusting the refractive index of select regions of the lens, post-operative refractive errors resulting from pre-operative measurement errors, variable lens positioning during implantation, and wound healing (aberrations) can be corrected or fine tuned in-situ.

For instance, cataract surgery typically requires that the natural lens of each eye be replaced with an IOL. Following insertion of the IOL, the surgeon can correct for aberrations resulting from the surgery or correct for slight misplacement of the IOL. Following surgery, and after allowing time for the wound to heal, the patient would return to the surgeon or an ophthalmic practitioner to have select regions of the IOL irradiated. These irradiated regions would experience a positive change in refractive index, which would correct for the aberrations as well as the patient's needs for vision correction. In some instances, the surgeon would be able to adjust the IOL in one eye for distance and adjust the IOL in the opposite eye for reading.

Typically, the irradiated portions of the optical, hydrogel polymeric material will exhibit a positive change in refractive index of about 0.01 or more. In one embodiment, the refractive index of the region will increase by about 0.03 or more. We have measured a positive change in refractive index in a hydrated, Akreos® IOL material of about 0.06.

It is to be understood by one of ordinary skill in the art, that an embodied method modifies the refractive properties of the material not by casting an optical material with non-reacted monomer (refraction modulation composition) followed by laser irradiation to promote additional polymerization chemistry as described in the aforementioned Calhoun Patent, but rather by a change in the refractive index of an already completely polymerized optical material. The term "completely polymerized" when used to characterize the optical materials used in the disclosed method means that the optical materials are 95% or more polymerized. One way to measure the completeness of a polymerized optical material is by near infrared spectroscopy, which is used to qualitatively determine the vinyl content of the material. Simple gravimetric weight analysis can also be used.

In an exemplary aspect, the irradiated regions of the optical, polymeric material can be defined by two- or three-dimensional structures. The two- or three-dimensional structures can comprise an array of discrete cylinders. Alternatively, the two- or three-dimensional structures can comprise a series of lines, or a combination of an array of cylinders and a series of lines. Moreover, the two- or three-dimensional structures can comprise area or volume filled structures, respectively. These area or volume filled structures can be formed by continuously scanning the laser at a constant scan rate over a selected region of the polymeric material. Nanometer-sized structures can also be formed by the zone-plate-array lithography method describe by R. Menon et al., *Proc. SPIE*, Vol. 5751, 330-339 (May 2005); *Materials Today*, p. 26 (February 2005).

In one embodiment, the irradiated regions of the optical polymer are defined by a series of line segments in a two dimensional plane having a line width from 0.2 µm to 5 µm, more particularly a line width from 0.6 µm to 3 µm and a height from 0.4 µm to 8 µm, more particularly a height from 1.0 µm to 4 µm (height is measured in the z direction of the material, which is parallel to direction of the laser light). For example, one can generate a segment array comprising a plurality of line segments with each line segment of any desired length, about 0.8 µm to about 3 µm in width and about 2 µm to 5 µm in height. The line segments can be separated by as little as 1.0 µm (0.5 µm spacing)??, and any number of line segments can be incorporated into the material. Moreover, the segment array can be positioned at any selected depth (z-direction), and any number of segment arrays can be generated at various depths into the material.

Figure 1B:
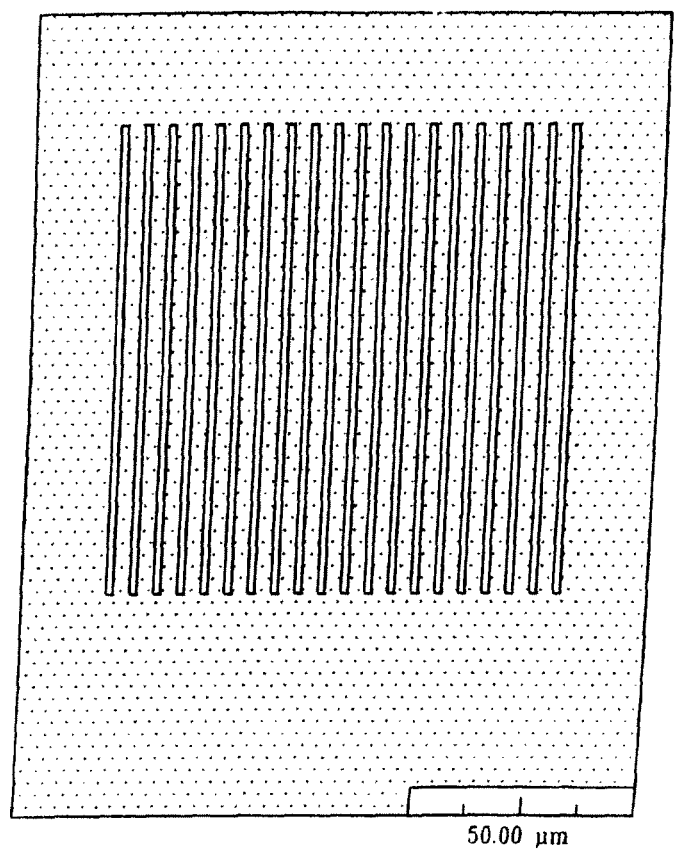
FIG. 1B is a schematic representation of the microscope photograph of FIG. 1A.

FIG. 1A is a microscope photograph with contrasting background of a line segment array comprising 20 lines written into an optical material. FIG. 1B is a schematic representation of the microscope photograph of FIG. 1A. Each line segment is about 100 μm in length, about 1 μm in width, with an intersegment separation of about 5 μm. The line segments have a height of about 3 μm and were written into the material at a distance of about 100 μm from the top surface of the material. Similar microscope photographs exhibiting line segment arrays were obtained at a distance of about 200 μm and 400 μm from the top surface of the material, thereby demonstrating that refractive structures can be written into the optical material at any selected depth.

Figure 2A:
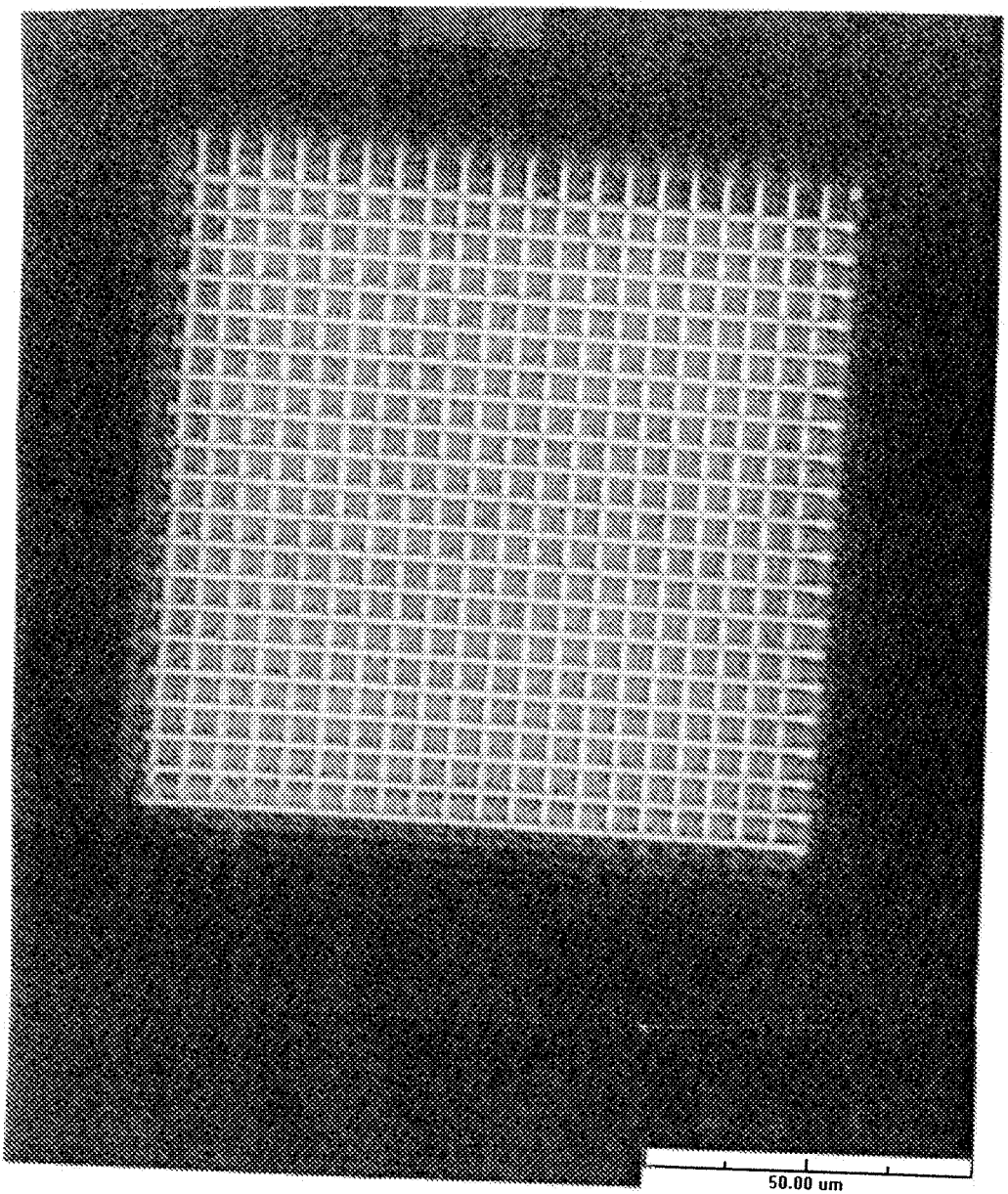
FIG. 2A is a microscope photograph of a line grating written above and orthogonal to another line grating in an optical, polymeric material produced by laser irradiation.
Figure 2B:
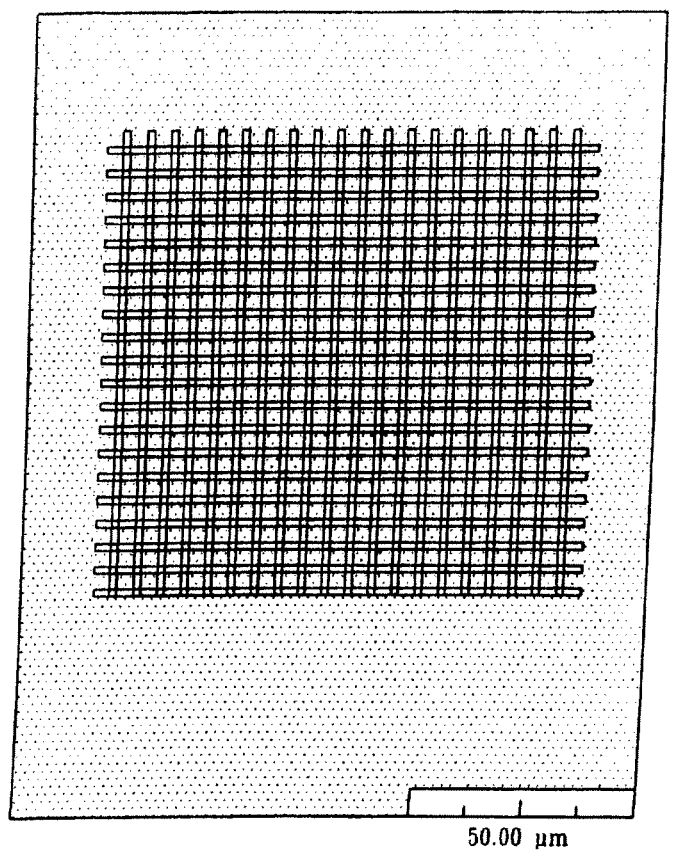
FIG. 2B is a schematic representation of the microscope photograph of FIG. 2B.

FIG. 2A is a microscopic photograph with contrasting background of one segment array written above and orthogonal to another segment array. FIG. 2B is a schematic representation of the microscope photograph of FIG. 2A. Each of the arrays has a similar dimensional structure to that described for FIG. 1 above. One segment array is positioned about 100 μm into the material, and the other segment array is positioned about 110 μm into the material for a center-line, segment array separation of about 10 μm. Again, each of these segment arrays has a height (depth) of about 3 μm, thus providing an intersegment separation in z of about 7 μm.

Figure 3A:
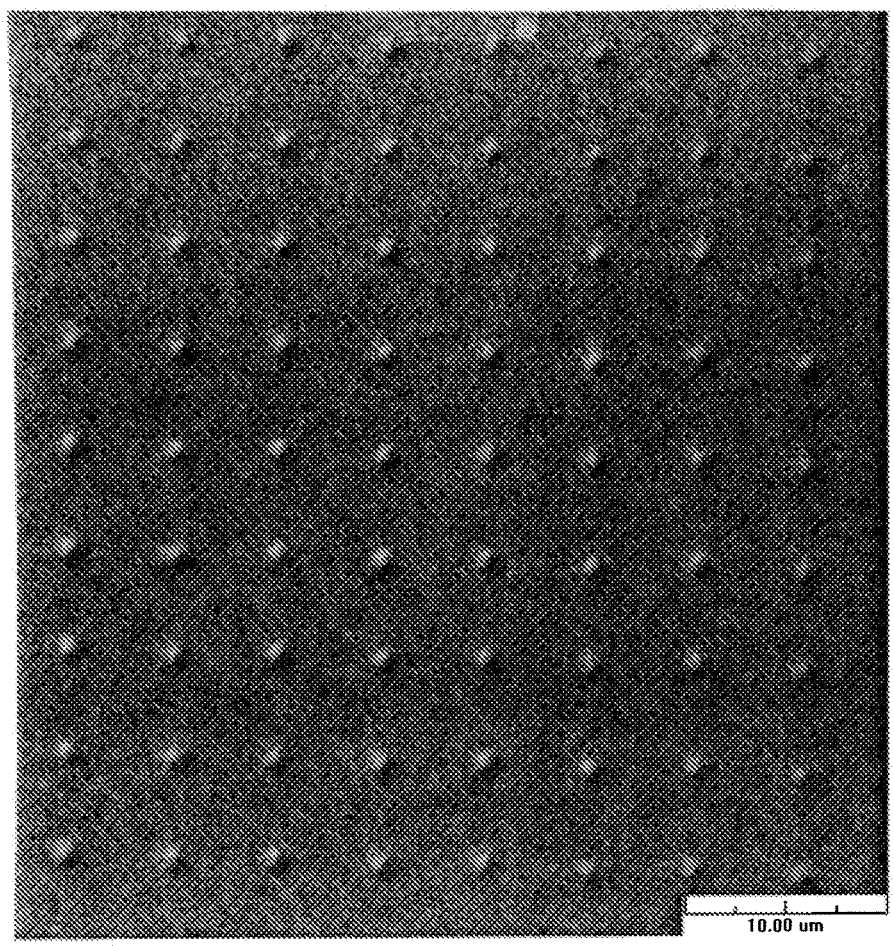
FIG. 3A is a microscope photograph of an array of cylinders etched in an optical, polymeric material produced by laser irradiation.
Figure 3B:
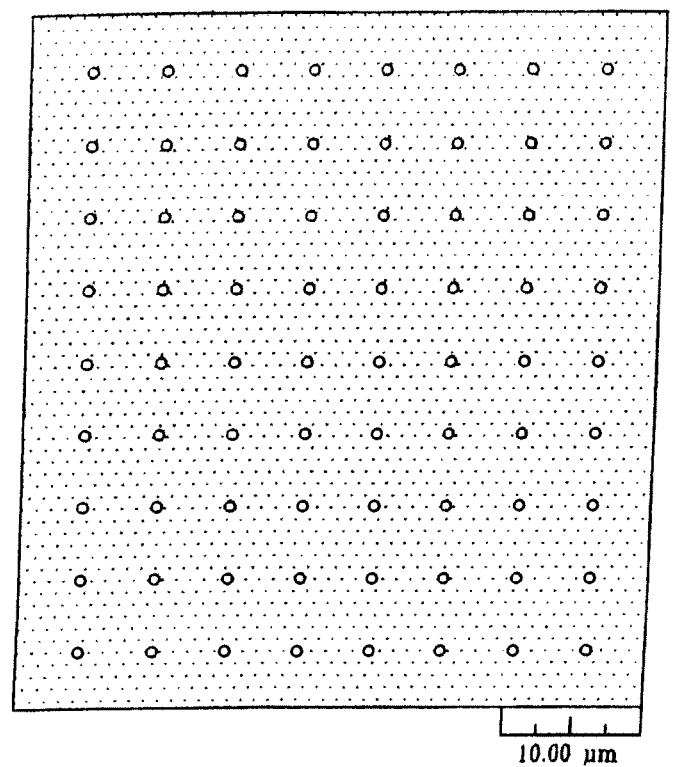
FIG. 3B is a schematic representation of the microscope photograph of FIG. 3A.

FIG. 3A is a microscopic photograph with contrasting background of an array of cylinders written into an optical material. FIG. 3B is a schematic representation of the microscope photograph of FIG. 3A. Each cylinder is about 1 μm in diameter with a height of about 3 μm. The cylinders are separated by about 5 μm. The cylinders were laser-etched into the material at a distance of about 100 μm from the top surface of the material.

Figure 4A:
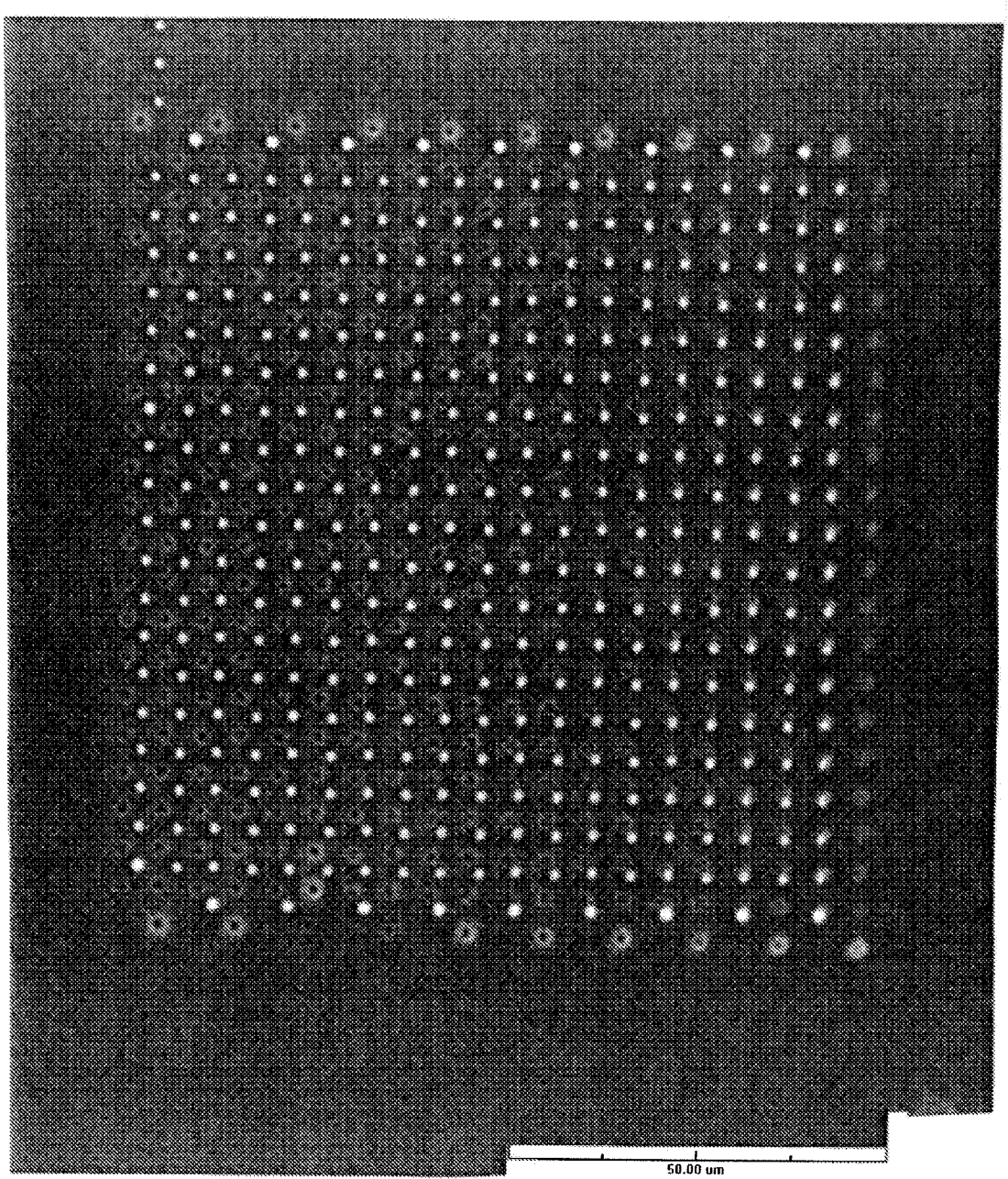
FIG. 4A is a microscope photograph of one array of cylinders (20×20) etched above and slightly offset to another array of cylinders (20×20) in an optical, polymeric material produced by laser irradiation.
Figure 4B:
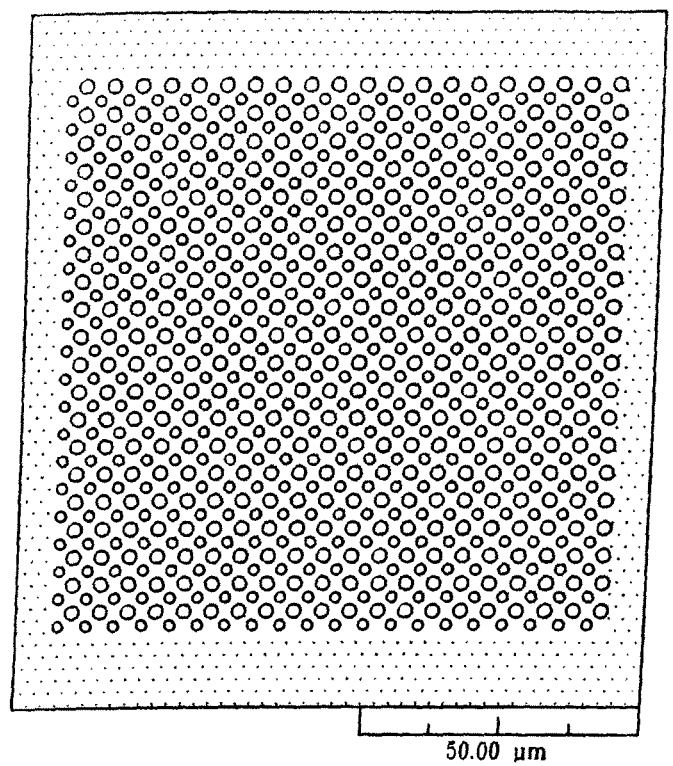
FIG. 4B is a schematic representation of the microscope photograph of FIG. 4A.

FIG. 4A is a microscopic photograph with contrasting background of one array of cylinders (20×20) written above and slightly offset to another array of cylinders (20×20). FIG. 4B is a schematic representation of the microscope photograph of FIG. 4A. Each of the cylinders has a similar dimensional structure to that described for FIG. 3 above. One array is positioned about 100 μm into the material, and the other array is positioned about 105 μm into the material for a center-line separation of about 5 μm. Each of the cylinders has a height (depth) of about 3 μm.

Figure 5:
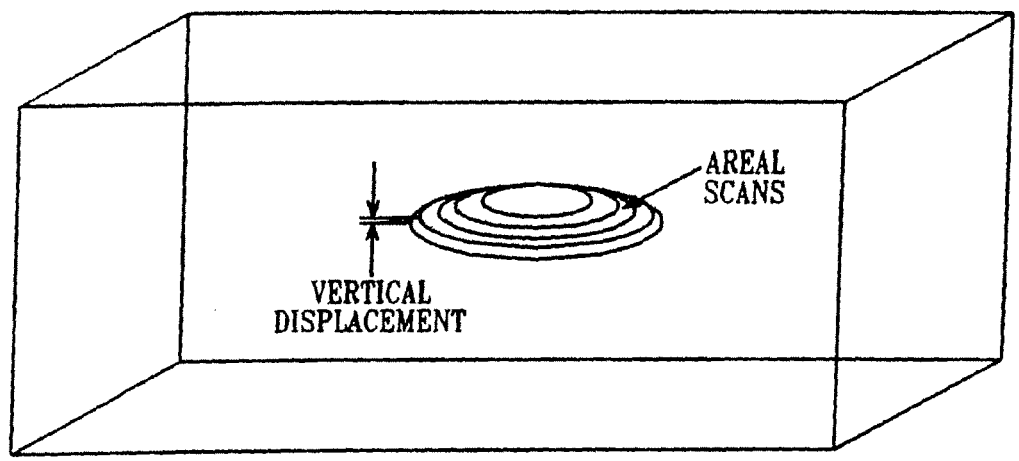
FIG. 5 is a schematic representation of a three-dimensional structure in an optical, polymeric material that can be produced by laser irradiation.
Figure 6:
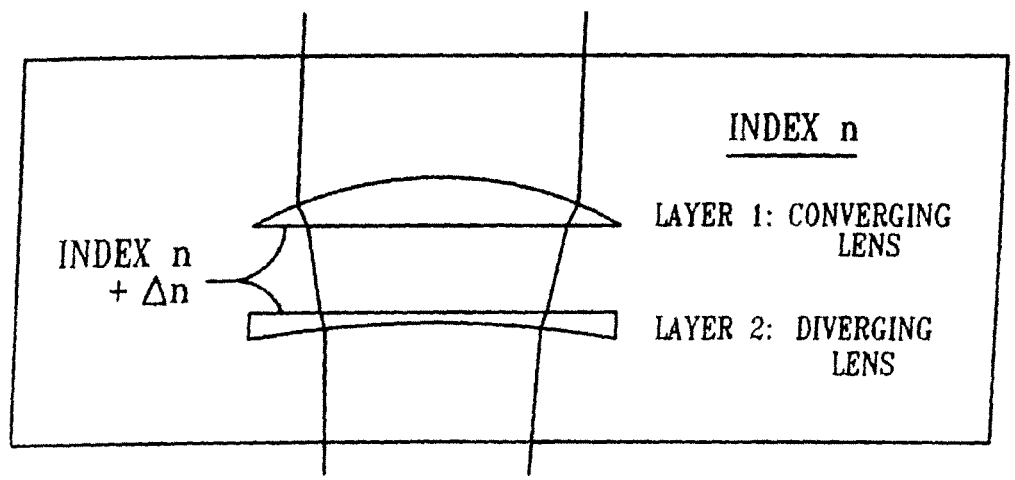
FIG. 6 is a schematic representation of creating a convex, plano or concave structure in an optical, polymeric material to yield a positive or negative correction.

The area-filled or volume-filled two- or three-dimensional structures can be formed by continuously scanning the laser at a constant scan rate over selected regions of the optical, polymeric material. As described, refractive structures can be written within the volume of an optical polymer material by repeatedly scanning a tightly focused beam of femtosecond pulses in selected regions creating a plurality of line segments. The volume of a line segment can be changed correspondingly with the depth of the scan, so as to produce three-dimensionally-shaped lenses with spheric, aspheric, toroidal or cylindrical shapes as shown in FIG. 5. Although the refractive index change is positive (+0.02 to +0.06), these refractive corrective lenses can be made in various combinations of convex, plano-, or concave to yield a positive correction or negative correction, as shown in FIG. 6. The refractive structures can be stacked vertically, written separately in different planes, so as to act as a single lens element. Additional refractive structures can be written as desired.

As indicated by the micrographs of the refractive structures described as area-filled or volume-filled two- or three-dimensional structures, one can create a pattern of lines, cylinders and radial patterns in optical materials; however, it is also possible to create other optical features using the irradiation method described herein. For example, arrays of dots (e.g., having a dimension in the nanometer range) can be created by directing the laser beam at discrete points or spots within the material. Such an array can be arranged substantially on one plane or several such arrays can be created at different depths within the material. A material thus modified can be advantageously useful when light is not substantially scattered by the dots.

In one aspect, the refractive structures are formed proximate to the top anterior surface of an intraocular lens. For example, a positive or negative lens element (three-dimensional) is formed within a 300 μm volume, or within a 100 μm volume, from the anterior surface of the lens. The term "anterior surface" is the surface of the lens that faces the anterior chamber of a human eye.

A Laser and Optical Configuration for Modifying an Optical Material

Figure 7:
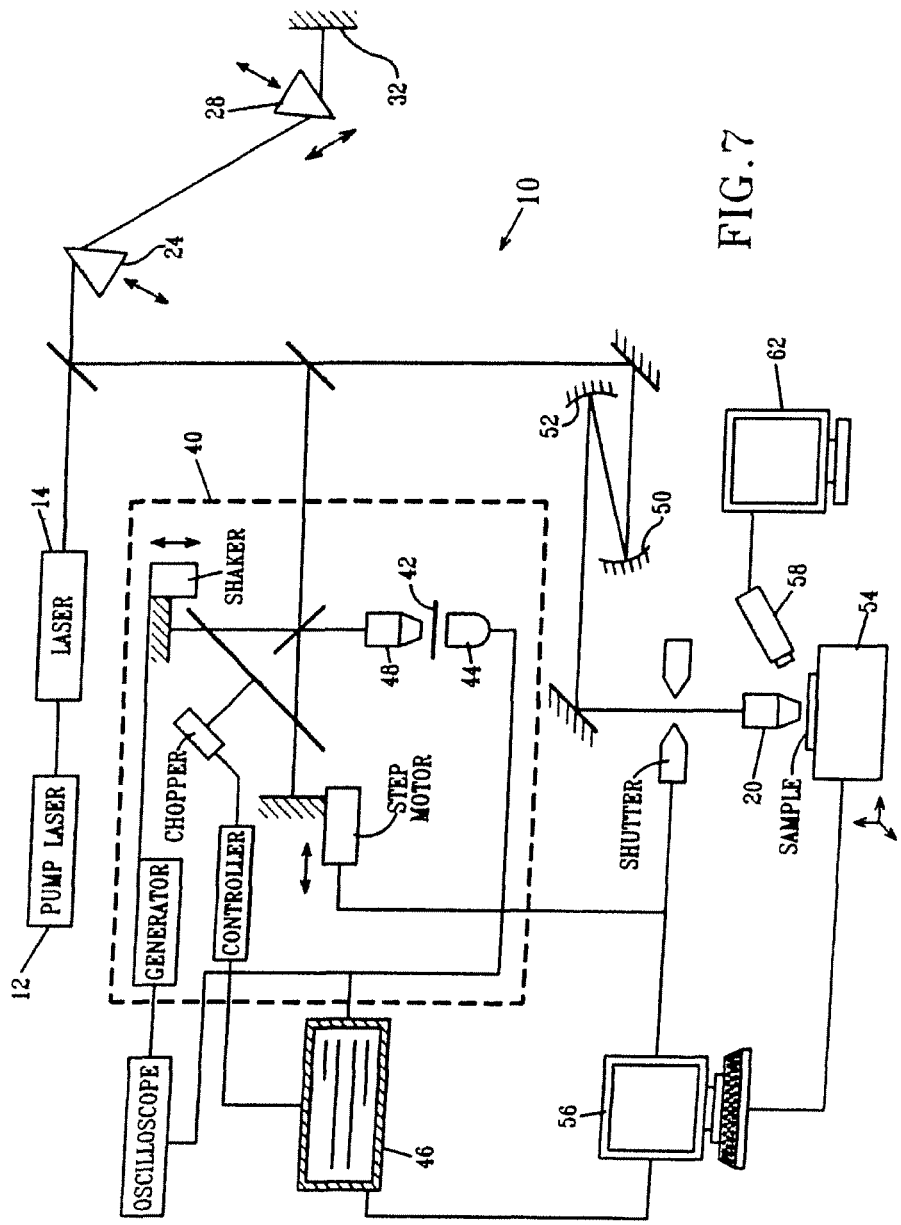
FIG. 7 is a schematic representation of the laser and optical system used to write the structures shown in FIGS. 1 to 4, 9, 10 and 12.

A non-limiting embodiment of a laser system 10 for irradiating an optical, polymeric material with a laser to modify the refractive index of the material in select regions is illustrated in FIG. 7. A laser source comprises a Kerr-lens mode-locked Ti:Sapphire laser 12 (Kapteyn-Murnane Labs, Boulder, Colo.) pumped by 4 W of a frequency-doubled Nd:YVO4 laser 14. The laser generates pulses of 300 mW average power, 30 fs pulse width, and 93 MHz repetition rate at wavelength of 800 nm. Because there is a reflective power loss from the mirrors and prisms in the optical path, and in particular from the power loss of the objective 20, the measured average laser power at the objective focus on the material is about 120 mW, which indicates the pulse energy for the femtosecond laser is about 1.3 nJ.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity compensation scheme is used to provide the negative dispersion that compensates for the positive dispersion introduced by the focusing objective. Two SF10 prisms 24 and 28 and one ending mirror 32 form a two-pass, one-prism-pair configuration. In a particular instance, Applicants used a 37.5 cm separation distance between the prisms to compensate for the positive dispersion of the microscope objective and other optics within the optical path.

A collinear autocorrelator 40 using third-order harmonic generation is used to measure the pulse width at the objective focus. Both $2^{nd}$ and $3^{rd}$ harmonic generation have been used in autocorrelation measurements for low NA or high NA objectives. Applicants also selected third-order surface harmonic generation (THG) autocorrelation to characterize the pulse width at the focus of the high-numerical aperture (NA) objectives because of its simplicity, high signal to noise ratio, and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, a transform-limited 27 fs duration pulse is used, which is focused by a 60×0.70NA Olympus LUCPlanFLN long-working-distance objective 48.

Because the laser beam will spatially diverge after it comes out of the laser, a concave mirror pair 50 and 52 is added into the optical path in order to adjust the dimension of the laser beam so that the laser beam can optimally fill the objective aperture. A 3D 100 nm resolution DC servo motor stage 54 (Newport VP-25xA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micromachine different patterns in the materials using different scanning speeds at different position or depth in the optical material, and different laser exposure times. In addition, a CCD camera 58 along with a monitor 62 is used beside the objective 20 to monitor the process in real time.

The method and optical apparatus described above can be used to modify the refractive index of an intraocular lens following the surgical implantation of the intraocular lens in a human eye (or before the lens is implanted in an eye).

Accordingly, an embodiment of the invention is directed to a method comprising identifying and measuring the aberrations resulting from the surgical procedure of providing a patient with an IOL. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemers disk, the Shack Hartmann wavefront sensor, the Hartmann screen, and the Fizeau, and Twyman-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the refractive structures to be written into the lens material to correct for those aberrations or to provide vision correction to the patient. These computer programs are well known to those of ordinary skill in the art. The computer then communicates with the laser-optical system and select regions of the lens are irradiated with a laser having a pulse energy from 0.05 nJ to 1000 nJ as described herein.

The Optical, Hydrogel Polymeric Materials

The optical, hydrogel polymeric materials that can be irradiated with a laser according to the methods described in this application can be any optical, hydrogel polymeric material known to those of ordinary skill in the polymeric lens art, particularly those in the art familiar with optical polymeric materials used to make intraocular lenses. Non-limiting examples of such materials include those used in the manufacture of ophthalmic devices, such as siloxy-containing polymers, acrylic, hydrophilic or hydrophobic polymers or copolymers thereof. The forming of the refractive structures is particularly suited for modifying the refractive index in select and distinct regions of a polymeric, optical silicone hydrogel, or a polymeric, optical non-silicone hydrogel.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will have a relatively high refractive index of approximately 1.40 or greater, particularly 1.48 or greater. Many of these materials are also characterized by a relatively high elongation of approximately 80 percent or greater.

In one embodiment, the optical polymeric materials are prepared as a copolymer from at least three monomeric components. The first monomeric component, preferably a monomeric component with aromatic functionality, is present in the copolymer in an amount of at least 60% by weight, and its homopolymer will have a refractive index of at least 1.50, particularly at least 1.52 or at least 1.54. The second monomeric component, preferably, an alkyl(meth)acrylate, is present in the copolymer in an amount from 3% to 20% or from 3% to 10%, by weight. The first and second monomeric components together represent at least 70% by weight of the copolymer. The term "homopolymer" refers to a polymer that is derived substantially completely from the respective monomeric component. Minor amounts of catalysts, initiators, and the like can be included, as is conventionally the case, in order to facilitate the formation of the homopolymer.

Particularly useful first monomeric components include styrene, vinyl carbazole, vinyl naphthalene, benzyl(meth)acrylate, phenyl(meth)acrylate, naphthyl(meth)acrylate, 2-phenoxyethyl(meth)acrylate, 2,3-dibromopropyl-(meth)acrylate and any one mixture thereof. Particularly useful second monomeric components include n-butyl(meth)acrylate, n-hexyl(meth)acrylate, 2-ethylhexyl-(meth)acrylate, 2-ethoxyethyl(meth)acrylate, 2,3-dibromopropyl(meth)acrylate, 1,1-dihydroperfluorobutyl(meth)acrylate and any one mixture thereof.

The third monomeric component is a hydrophilic monomeric component. The hydrophilic component is present in an amount, from 2% to 30% by weight of the copolymer. The hydrophilic component is particularly present in an amount of less than about 20% by weight of the copolymer. Copolymers that include about 10% by weight or more of a hydrophilic monomeric component tend to form hydrogels if placed in an aqueous environment. The term "hydrophilic monomeric component" refers to compounds that produce hydrogel-forming homopolymers, that is, homopolymers which become associated with at least 25% of water, based on the weight of the homopolymer, if placed in contact with an aqueous solution.

Specific examples of useful hydrophilic monomeric components include N-vinyl pyrrolidone; hydroxyalkyl(meth)acrylates such as 2-hydroxyethyl(meth)acrylate, 3-hydroxypropyl(meth)acrylate, 2-hydroxypropyl(meth)acrylate, 4-hydroxybutyl (meth)acrylate, 2,3-dihydroxypropyl(meth)acrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

In another embodiment, the optical polymeric materials are prepared as a copolymer from at least two monomeric components and a photosensitizer. The photosensitizer can be polymerizable or be entrapped within the formed polymer. The first monomeric component is a hydrophilic monomeric component. The hydrophilic component is present in an amount from 50% to 90% by weight of the copolymer. The hydrophilic component is particularly present in an amount of 60% to 85% by weight of the copolymer. The second monomeric component, preferably, an alkyl(meth)acrylate, is present in the copolymer in an amount from 5% to 20% or from 3% to 10%, by weight. The first and second monomeric components together represent at least 90% by weight of the copolymer.

The polymeric optical materials will likely include a crosslink component that can form crosslinks with at least the first or the second monomeric components–. Advantageously, the crosslink component is multi-functional and can chemically react with both the first and second monomeric components. The crosslink component is often present in a minor amount relative to the amounts of the first and second monomeric components. Particularly, the crosslink component is present in a copolymer in an amount of less than about 1% by weight of the copolymer. Examples of useful crosslink components include ethylene glycol dimethacrylate, propylene glycol dimethacrylate, ethylene glycol diacrylate and the like and mixtures thereof.

In one aspect, the optical, polymeric materials can be prepared from one or more aromatic (meth)acrylate monomers having the formula:

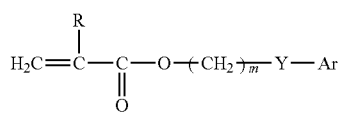

wherein: R is H or $CH_3$; m is an integer selected from 0 to 10; Y is nothing, O, S, or $NR^1$, wherein $R^1$ is H, $CH_3$, $C_2$-$C_6$alkyl, iso-$OC_3H_7$, phenyl or benzyl; Ar is any aromatic ring, e.g., phenyl, which can be unsubstituted or substituted with H, $CH_3$, $C_2H_5$, n-$C_3H_7$, iso-$C_3H_7$, $OCH_3$, $C_6H_{11}$, Cl, Br, phenyl or benzyl; and a crosslinking component.

Exemplary aromatic (meth)acrylate monomers include, but are not limited to: 2-ethylphenoxy(meth)acrylate, 2-ethylthiophenyl(meth)acrylate, 2-ethylaminophenyl (meth) acrylate, phenyl-(meth)acrylate, benzyl(meth)acrylate, 2-phenylethyl(meth)acrylate, 3-phenylpropyl-(meth)acrylate, 4-phenylbutyl(meth)acrylate, 4-methylphenyl(meth) acrylate, 4-methylbenzyl(meth)acrylate, 2-2-methylphenylethyl (meth)acrylate, 2-3-methylphenylethyl(meth)acrylate, 2-4-methylphenylethyl (meth)acrylate, 2-(4-propylphenyl) ethyl(meth)acrylate, 2-(4-(1-methylethyl)phenyl)ethyl methacrylate, 2-(4-methoxyphenyl)ethyl methacrylate and the like.

Generally, if the optical, polymeric material is prepared with both an aromatic acrylate and an aromatic methacrylate as defined by the formula above, the materials will generally comprise a greater mole percent of aryl acrylate ester residues than of aryl methacrylate ester residues. It is preferred that the aryl acrylate monomers constitute from about 20 mole percent to about 60 mole percent of the polymer, while the aryl methacrylate monomers constitute from about 5 mole percent to about 20 mole percent of the polymer. Most advantageous is a polymer comprising about 30-40 mole percent 2-phenylethyl acrylate and about 10-20 mole percent 2-phenylethyl methacrylate. Hydrophilic monomer is also present in about 20-40 mol percent.

In another aspect, the optical, polymeric materials will have a fully hydrated (equilibrium) water content from 5% to 15% by weight, which also helps to minimize the degree of hazing following thermal stress as described, as well as minimize the formation of water vacuoles in-vivo. To achieve the desired water content, one may include a hydrophilic, aromatic monomer having a formula, G-D-Ar, wherein Ar is a $C_6$-$C_{14}$ aromatic group having a hydrophilic substituent, in the polymerizable compositions. D is a divalent linking group, and G is a polymerizable ethylenic site.

One particular hydrophilic aromatic monomer is represented by the formula

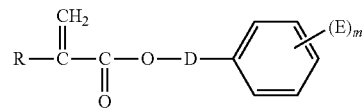

wherein R is hydrogen or $CH_3$; D is a divalent group selected from the group consisting of straight or branched $C_1$-$C_{10}$ hydrocarbons and an alkyleneoxide (e.g., —($CH_2CH_2O$)$_n$—), and E is selected from the group consisting of hydrogen (if D is alkyleneoxide), carboxy, carboxamide, and monohydric and polyhydric alcohol substituents. Exemplary hydrophilic substituents include, but are not limited to, —COOH, —$CH_2$—$CH_2OH$, —(CHOH)$_2CH_2OH$, —$CH_2$—CHOH—$CH_2OH$, poly(alkylene glycol), —C(O)O—$NH_2$ and —C(O)—N(CH$_3$)$_2$.

Exemplary hydrophilic, aromatic monomers are represented by the following

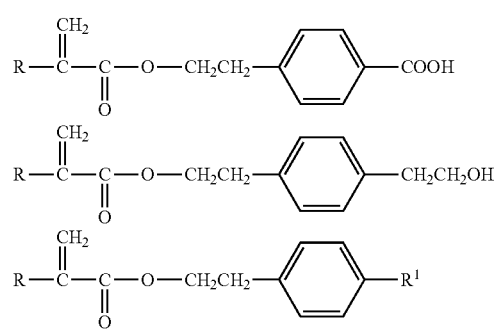

wherein R is hydrogen or $CH_3$ and $R^1$ is —C(O)O—$NH_2$ or —C(O)—N(CH$_3$)$_2$.

In another aspect, the optical, polymeric material is prepared from a first aromatic monomeric component, which is present in 5-25% by weight, the second monomeric component is a hydrophilic monomeric component, e.g., 2-hydroxyethyl(meth)acrylate, which is present from 30 to 70% by weight; and 5 to 45% by weight of a another alkyl (meth) acrylate selected from the group consisting of methyl(meth) acrylate, ethyl (meth)acrylate, propyl(meth)acrylate, butyl (meth)acrylate, pentyl(meth)acrylate, hexyl meth)acrylate, heptyl(meth)acrylate, nonyl(meth)acrylate, stearyl meth) acrylate, octyl (meth)acrylate, decyl(meth)acrylate, lauryl (meth)acrylate, pentadecyl(meth)acrylate and 2-ethylhexyl (meth)acrylate. Among the alkyl(meth)acrylates, those containing 1 to 3 carbon atoms of alkyl group are particularly advantageous.

Exemplary aromatic monomeric components include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

In another aspect, the optical, polymeric material is prepared from a hydrophilic acrylic that comprises about 90% (by weight) N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. Another hydrophilic acrylic of interest is referred to as HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water.

One particular hydrophilic, acrylic material of interest is based upon a commercially available IOL sold in the market by Bausch & Lomb under the trade name Akreos®. This acrylic material comprises about 80% by weight HEMA and 20 wt % MMA.

The optical, polymeric material can also be prepared by copolymerizing a specific monomer mixture comprising perfluorooctylethyloxypropylene (meth)acrylate, 2-phenylethyl (meth)acrylate, an alkyl(meth)acrylate monomer having the following general formula,

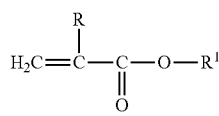

wherein R is hydrogen or methyl and $R^1$ is a linear or branched $C_4$-$C_{12}$ alkyl group, hydrophilic monomer and a crosslinking monomer. An exemplary list of alkyl (meth) acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene (meth)acrylate is present from 5% to 20% by weight, the 2-phenylethyl(meth) acrylate is present from 20% to 40% by weight, the alkyl (meth)acrylate monomer is present from 20% to 40% by weight, the hydrophilic monomer is present from 20% to 35%, and the crosslinking agent is present from 0.5% to 2% by weight.

The optical, polymeric component will likely include a crosslinking agent. The copolymerizable crosslinking agent(s) useful in forming the copolymeric material of the invention include any terminally ethylenically unsaturated compound having more than one unsaturated group. Particularly, the crosslinking agent includes a diacrylate or a dimethacrylate. The crosslinking agent may also include compounds having at least two (meth)acrylate and/or vinyl groups. Particularly advantageous crosslinking agents include diacrylate compounds.

The optical, polymeric materials are prepared by generally conventional polymerization methods from the respective monomeric components. A polymerization mixture of the monomers in the selected amounts is prepared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butulcyclohexyl) peroxydicarbonate, azonitriles, such as azobisisobytyronitrile, and the like. A particular initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

EXAMPLES

Example 1

Preparation of Akreos IOL with 17% Coumarin-1

Coumarin 1 dye (2.5 g) is dissolved in an ethanol-water mixture containing 10 mL ethanol and 5 mL water. Dry weight of the Akreos sample is recorded. The samples are hydrated in pure water and the mass is recorded. Following the hydration step, the samples are soaked in the ethanol-water mixture containing the coumarin 1 dye until a constant mass is attained. The mass after soaking in the dye solution is recorded. Mass of the dye doped is calculated as the difference between the mass after soaking in the solution, and the dry mass multiplied by the mass concentration of the dye in the ethanol-water solution. Percentage of the dye doped is calculated as the ratio of mass of coumarin 1 dye doped over the dry mass multiplied by 100.

Example 2

Forming Structures in Akreos IOL Materials

The optical system described herein above was used to form line segments in select regions of optical materials. Experiments were conducted with Akreos IOL materials with and without photosensitizer. Akreos IOL materials comprise about 80 wt % HEMA and 20 wt % MMA with a water content of about 26% using similar process conditions described above.

The hydrated sample was mounted horizontally on the scanning platform, and the femtosecond laser beam was directed vertically downward through the high-numerical-aperture objective and was focused inside the bulk material, as shown in FIG. 7, at a depth of about 100 µm from the upper surface of the sample. Periodic gratings structures were created with a scanning speed of 0.4 µm/sec in an X-Y plane perpendicular to the laser beam. An Olympus BX51 Model microscope was used to observe the gratings that were created inside these three materials.

The microscope images indicate the formation of periodic parallel line segments inside the samples with 5-µm spacing. The segments are difficult to see in bright-field microscope, indicating that the segments exhibit low scattering. The line width of the segments is about 1 µm, which is significantly smaller than the laser focus diameter of 2.5 µm that was measured using a knife-edge method.

A cross section of the irradiated materials revealed that the cross section of a line segment was elliptical with the longer axis oriented in the direction of the laser beam, indicating that there was a larger laser intensity distribution in this direction.

By carefully adjusting the cover-slip correction of the objective, this spherical aberration could be minimized.

Figure 8A:
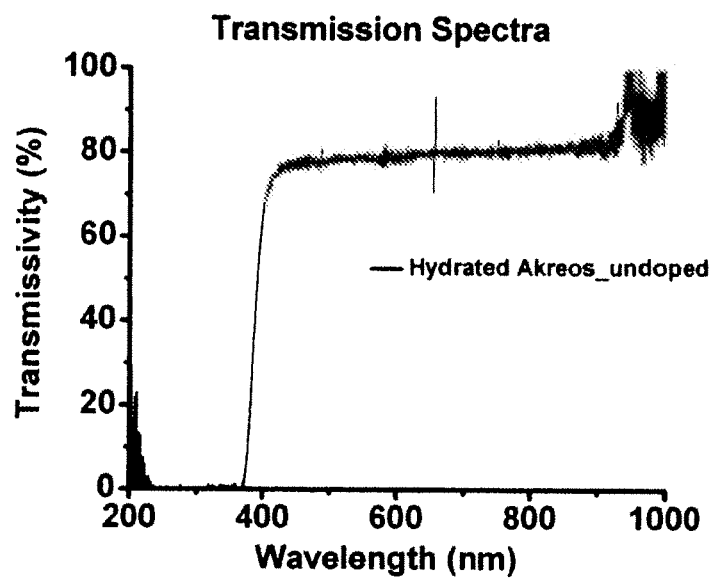
FIG. 8A is a transmission spectrum of a hydrated Akreos® IOL without photosensitizer.
Figure 8B:
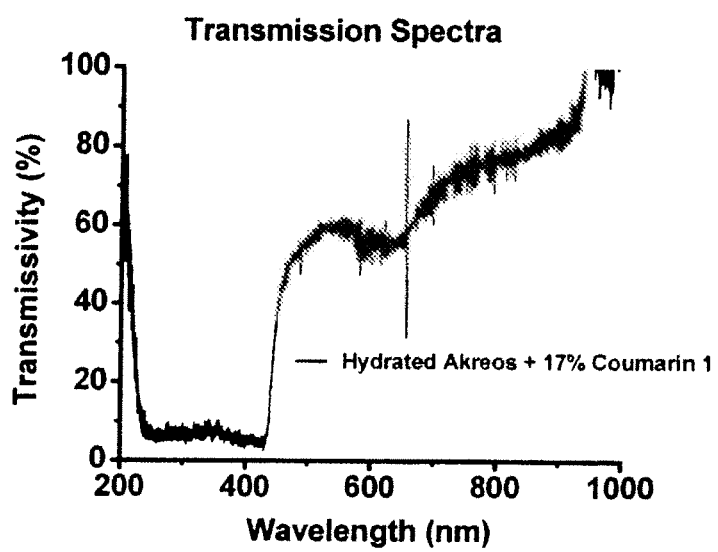
FIG. 8B is a transmission spectrum of a hydrated Akreos® IOL doped with a solution containing 17 wt. % coumarin-1.

As indicated in FIGS. 8A and 8B, the incorporation of coumarin-1 into an Akreos IOL provided a red shift in the transmission spectrum of an Akreos IOL material of about 50 nm. The Akreos IOL material with coumarin-1 has a relatively significant absorption profile at 400 nm and to about 425 nm, whereas an Akreos IOL material without photosensitizer is essentially transparent at these wavelengths.

Figure 9A:
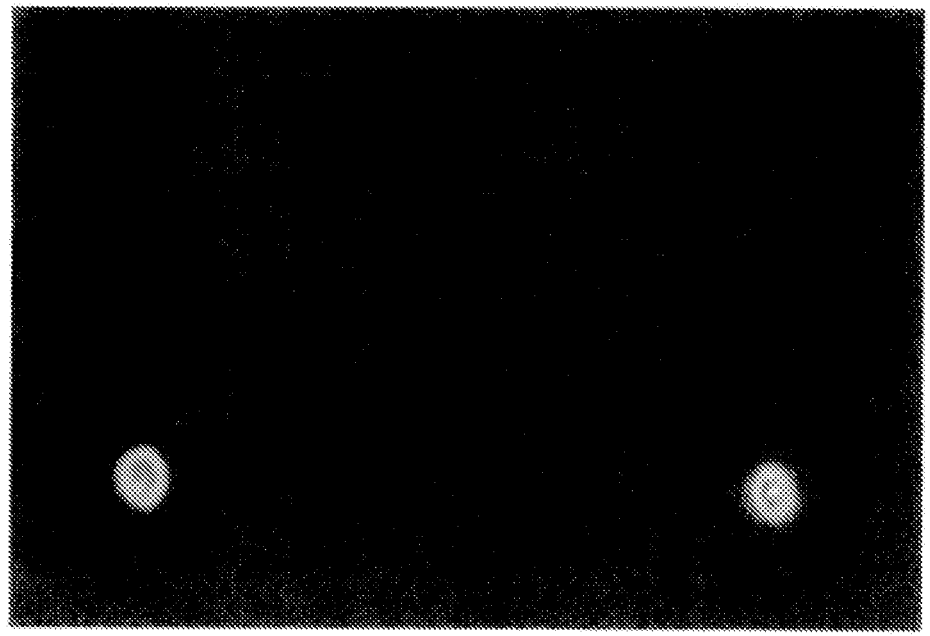
FIG. 9A is phase contrast photograph of a hydrated Akreos® IOL without photosensitizer micromachined at a scan rate of 50 m/s and 160 mW average power.
Figure 9B:
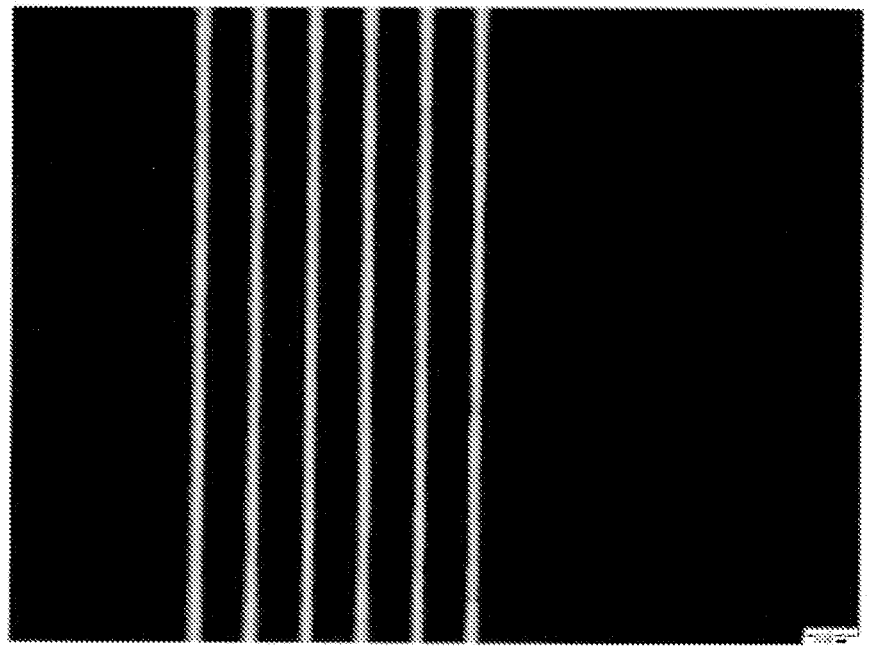
FIG. 9B is phase contrast photograph of a hydrated Akreos® IOL doped with a solution containing 17 wt. % coumarin-micromachined at a scan rate of 50 μm/s and 160 mW average power.

FIGS. 9A and 9B are phase contrast photographs of Akreos IOL materials with refractive line segments written within the materials at a depth of about 200 μm from the top irradiated surface. The irradiation process was conducted at 160 mW average power and a scan rate of 50 μm/s. As indicated in FIG. 9A, the refractive line segments written in the Akreos IOL material without photosensitizer provide little, if any, change in refractive index, $\Delta n \ll 0.005$ (visible detection limit of the structures). In fact, it is very difficult to see the refractive line segments in the material even with phase contrast enhancement. In contrast, as indicated in FIG. 9B, the refractive line segments written in the Akreos IOL material with 17% coumarin-1 at the identical power and scan rate provide a very significant change in refractive index, $\Delta n > 0.06$. The line segments are clearly visible with phase contrast enhancement.

Figure 10A:
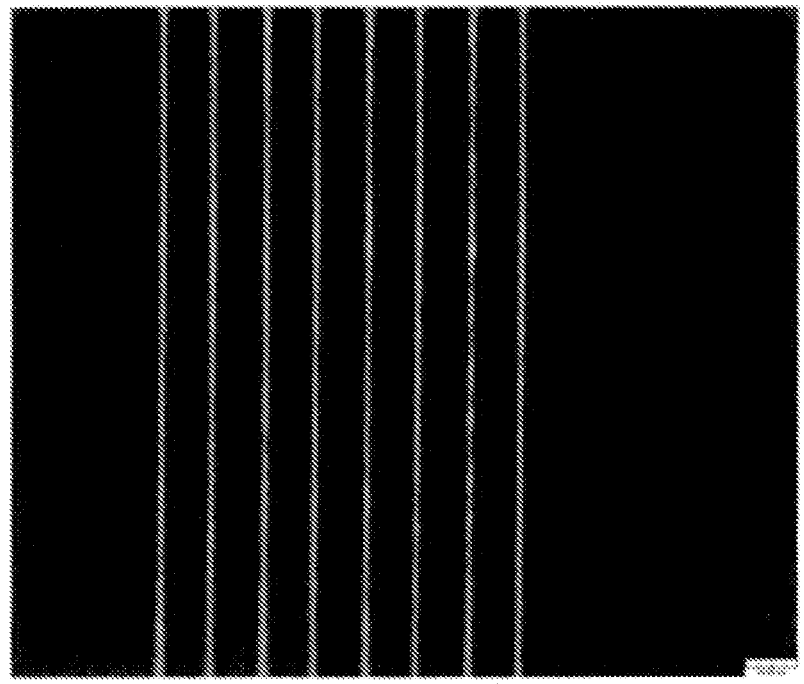
FIG. 10A is phase contrast photograph of a hydrated Akreos® IOL doped with a solution containing 17 wt. % coumarin-1 micromachined at a scan rate of 1 mm/s and 160 mW average power.
Figure 10B:
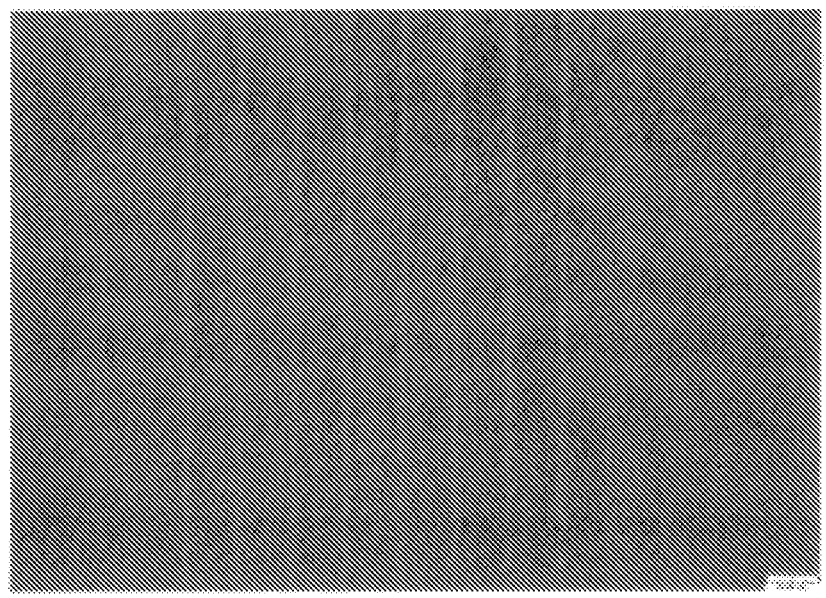
FIG. 10B phase contrast photograph of a hydrated Akreos® IOL doped with a solution containing 17 wt. % coumarin-1 micromachined at a scan rate of 1 mm/s and 60 mW average power.

FIGS. 10A and 10B indicate how differences in the refractive power of the written line segments (the magnitude of change in refractive index) can be varied based on the constant scan rate and laser power. FIG. 10A shows that one can form refractive line segments in Akreos IOL materials with 17% coumarin-1 at a scan rate of 1 mm/s, and with a $\Delta n$ of about 0.02 to 0.3. This is a surprising result since one would have to scan at about 10 μm/s to generate similar line segments with a $\Delta n$ of about 0.02 to 0.3 in an Akreos IOL material without photosensitizer. The presence of the coumarin-1 allows one to increase the scan rate nearly 100-fold. Moreover, even with a relatively low laser power, i.e., 60 mW, one can still generate refractive line segments with a $\Delta n$ of about 0.005.

Example 3

Preparation of Pure Vision® Silicone Hydrogel with 0.07 wt. % Fluorescein

Fluorescein (0.25 g) dye is dissolved in an ethanol-water mixture containing 50 mL ethanol and 50 mL water. Dry weight of the Pure Vision sample is recorded. The samples are hydrated in pure water and the mass is recorded. Following the hydration step, the samples are soaked in the ethanol-water mixture containing fluorescein dye until a constant mass is attained. The mass after soaking in the dye solution is recorded. Mass of the dye doped is calculated as the difference between the mass after soaking in the solution, and the dry mass multiplied by the mass concentration of the dye in the ethanol-water solution. Percentage of the dye doped is calculated as the ratio of mass of Fluorescein dye doped over the dry mass multiplied by 100.

Example 4

Forming Structures in Balafilcon A Silicone Hydrogel

The optical system as described in Example 2 was used to form line segments in select regions of hydrated balafilcon A (PureVision) silicone hydrogel materials. Experiments were conducted with and without the photosensitizer, fluorescein.

Figure 11A:
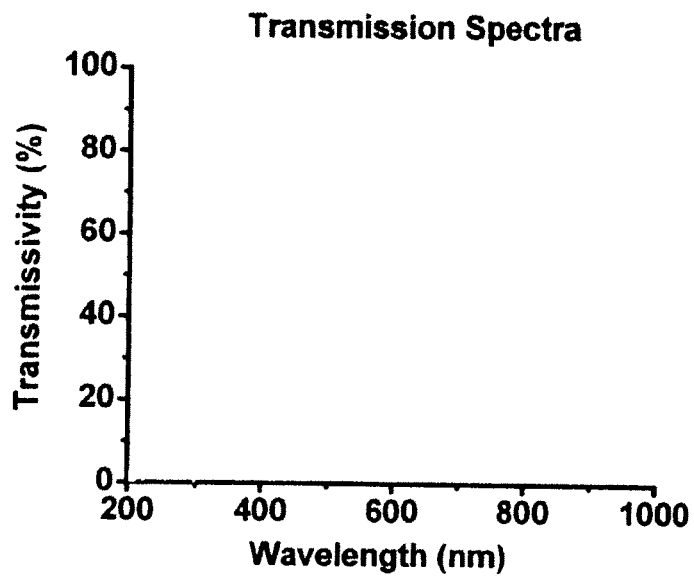
FIG. 11A is a transmission spectrum of a hydrated Pure Vision® silicone hydrogel without photosensitizer.
Figure 11B:
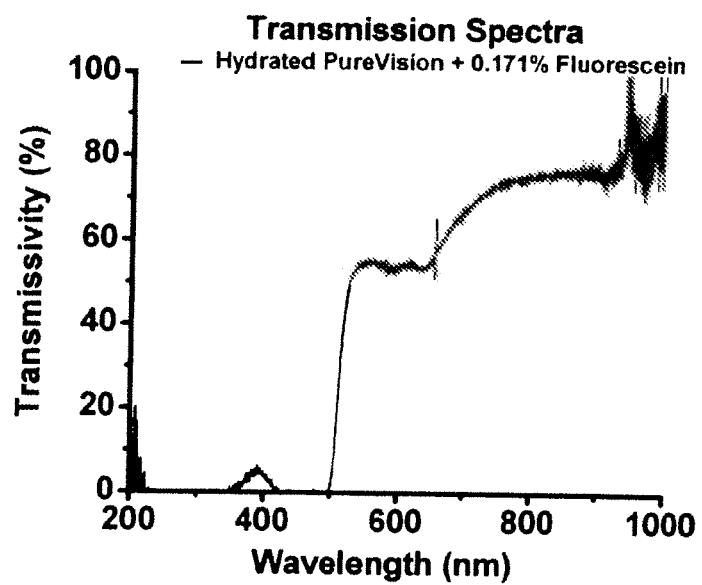
FIG. 11B is a transmission spectrum of a hydrated Pure Vision® silicone hydrogel doped with 0.17 wt. % fluorescein.

As indicated in FIGS. 11A and 11B, the incorporation of fluorescein into a balafilcon A silicone hydrogel provided a red shift in the transmission spectrum of at least 150 nm. The balafilcon A silicone hydrogel with fluorescein has a relatively significant absorption profile at 500 nm (FIG. 12B), whereas a silicone hydrogel without photosensitizer is essentially transparent at these wavelengths (FIG. 12A).

Figure 12A:
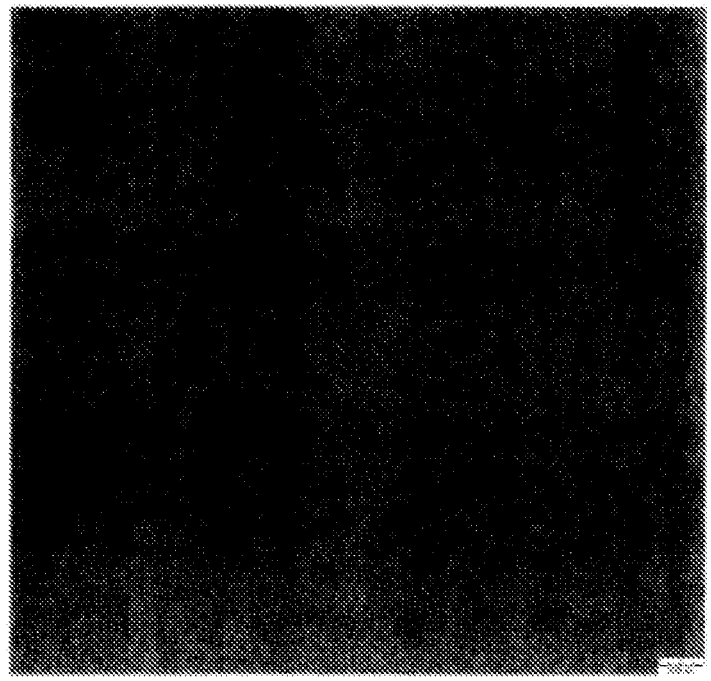
FIG. 12A is phase contrast photograph of a hydrated Pure Vision® silicone hydrogel without photosensitizer micromachined at a scan rate of 0.5 m/s and 60 mW average power.
Figure 12B:
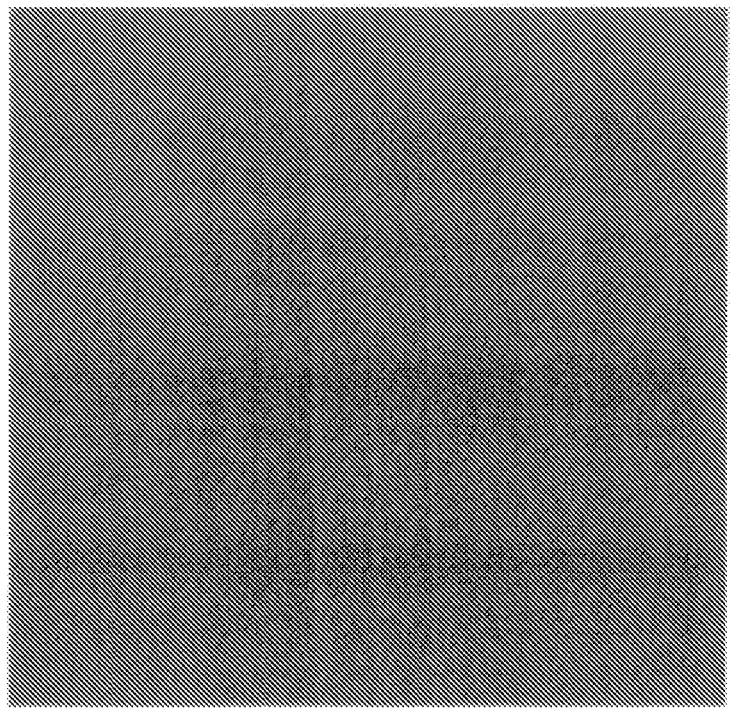
FIG. 12B is phase contrast photograph of a hydrated Pure Vision® silicone hydrogel doped with 0.17 wt. % fluorescein micromachined at a scan rate of 5.0 m/s and 60 mW average power.

FIG. 12A is phase contrast photograph of a balafilcon A silicone hydrogel that was micromachined at a depth of about 200 μm from the top irradiated surface. The irradiation process was conducted at 60 mW, and a constant scan rate of 0.5 μm/s. As indicated in FIG. 12A, the refractive line segments written in the balafilcon A silicone hydrogel without photosensitizer provide little, if any, change in refractive index, $\Delta n \ll 0.005$ (visible detection limit of the structures). In fact, it is very difficult to see the line segments in the material even with phase contrast enhancement. In contrast, as indicated in FIG. 12B, the refractive line segments written in the balafilcon A silicone hydrogel with 0.17 wt. % fluorescein at the identical power and at a constant scan rate of 5.0 μm/s (a ten-fold increase over the undoped balafilcon A) provide a very significant change in refractive index, $\Delta RI$ of about 0.02 to 0.03. The refractive line segments are clearly visible with phase contrast enhancement. Moreover, even with a relatively low laser power, i.e., 60 mW, one can still generate line segments with a $\Delta n$ of about 0.01 with a constant scan rate of 1 mm/s.

Figure 13:
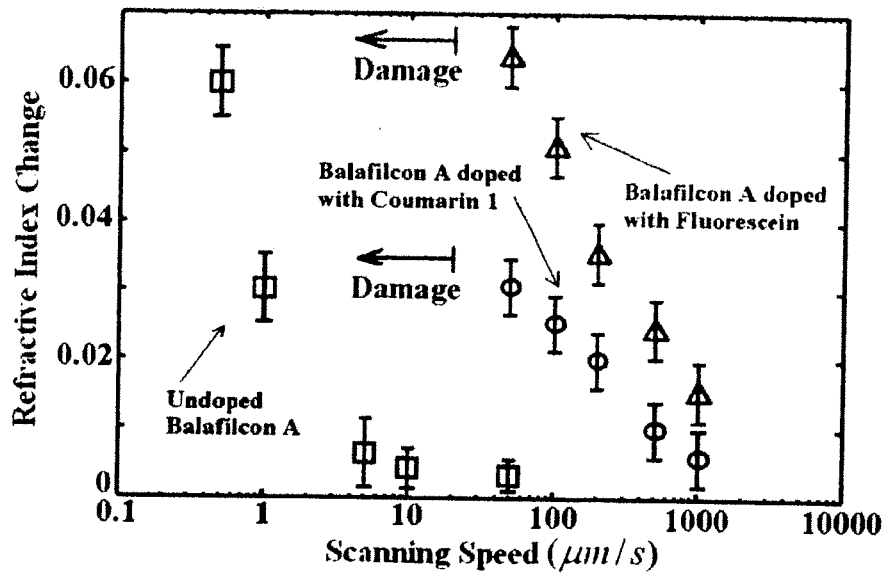
FIG. 13 is a plot of change in refractive index vs. scan rate in balafilcon A films (undoped and doped with fluorescein and coumarin-1.

FIG. 13 is a plot showing the change in refractive index vs. scan rate in balafilcon A materials; undoped or doped with fluorescein or coumarin-1. The plot demonstrates the significant enhancement of the photo-adjusting affect in the hydrogel material doped with a photosensitizer. The doping of the material permits one to increase the scan rate of the laser through the material, i.e., form refractive line segments in the material, by nearly 100-fold to achieve a comparable modification of the refractive index in the material.

In Examples 2 and 4, the refractive structures (line segment arrays) were investigated by focusing an unpolarized He—Ne laser beam with a wavelength of 632.8 nm on these arrays and monitoring the diffraction pattern. The diffraction angles showed good agreement with the diffraction equation $$m\lambda = d \sin \theta \tag{1}$$

where m is the diffraction order, $\lambda$ is the wavelength of the incident laser beam which here is 632.8 nm, and d is the grating period.

The diffraction efficiency of the written segment array can be measured, and since the efficiency is a function of the refractive index change, it may be used to calculate the refractive index change in the laser irradiation region. Consider the grating as a phase gating; its transmittance function could be written as $$t(x_0, y_0) = (e^{i\phi_2} - e^{i\phi_1}) rect\left(\frac{x_0}{a}\right) * \frac{1}{d} comb\left(\frac{x_0}{d}\right) + e^{i\phi_1} \tag{2}$$

where a is the grating line width, d is the groove spacing, $\phi_1$ and $\phi_2$ are the phase delays through the lines and ambient region respectively, $$\phi_2 = 2\pi \times \frac{(n + \Delta n) \times b}{\lambda} \text{ and } \phi_1 = 2\pi \times \frac{n \times b}{\lambda},$$

b is the thickness of the grating line, n is the average refractive index of the material, $\Delta n$ is the average refractive index change in the grating lines, and $\lambda$ is the incident light wavelength of the measurement (632.8 nm). Here, the grating line width is 1 μm and the thickness is 3 μm. The index change within the laser effect region can be approximated to be uniform. The convolution theorem can be used to calculate the spectrum of the grating such as $$T(f_u,f_v)=F\{t(x_0,y_0)\}=e^{1\phi_2}-e^{1\phi_1})a\ \sin\ c(af_x)\text{comb}(df_x)\delta(f_v)+e^{i\phi_1}\delta(f_u,f_v) \quad (3)$$

Then, the intensity distribution of the grating diffraction pattern is:

$$I(x,y)=\left(\frac{1}{\lambda z}\right)^2 \times \left[(e^{i\phi_2}-e^{i\phi_1})\frac{a}{d}\sum_{n=-\infty}^{\infty}\text{sinc}\left(\frac{an}{d}\right)\delta\left(\frac{x}{\lambda z}-\frac{n}{d},\frac{y}{\lambda z}\right)+e^{i\phi_1}\delta\left(\frac{x}{\lambda z},\frac{y}{\lambda z}\right)\right]^2 \quad (4)$$

From this formula, the intensity of the 0th ($I_0$), 1st ($I_1$), and 2nd ($I_2$) order diffraction light is $$I_0=\left(\frac{1}{\lambda z}\right)^2 \times \left[\left(e^{i2\pi\times\frac{(n+\Delta n)\times b}{\lambda}}-e^{i2\pi\times\frac{n\times b}{\lambda}}\right)\frac{a}{d}+e^{i2\pi\times\frac{n\times b}{\lambda}}\right]^2 \quad (5)$$

$$I_1=\left(\frac{1}{\lambda z}\right)^2 \times \left[\left(e^{i2\pi\times\frac{(n+\Delta n)\times b}{\lambda}}-e^{i2\pi\times\frac{n\times b}{\lambda}}\right)\frac{a}{d}\text{sinc}\left(\frac{a}{d}\right)\right]^2 \quad (6)$$

and $$I_2=\left(\frac{1}{\lambda z}\right)^2 \times \left[\left(e^{i2\pi\times\frac{(n+\Delta n)\times b}{\lambda}}-e^{i2\pi\times\frac{n\times b}{\lambda}}\right)\frac{a}{d}\text{sinc}\left(\frac{2a}{d}\right)\right]^2 \quad (7)$$

By comparing the light intensities of $1^{st}$, $2^{nd}$ and $0^{th}$ diffraction orders, the refractive index change within the grating lines can be determined. FIG. 3 shows the ratio of intensity of the $1^{st}$ and $2^{nd}$ diffraction order to $0^{th}$ order of the grating in PV2526-164 is 0.1374 and 0.0842 respectively, and the corresponding refractive index change determined by the analysis is about 0.06. Using the same method, we determined the average refractive index change in RD1817 and HEMA B to be 0.05±0.0005 and 0.03±0.0005. Thus, it was demonstrated that the refractive index of a material can be modified by applying an ultrafast laser thereto.

Example 5

A femtosecond laser oscillator with a Kerr-lens mode-locked Ti:Sapphire laser (MaiTai HP from Newport), generating pulses of 100 fs pulsewidth and 80 MHz repetition rate at a tunable wavelength range from 690 nm to 1040 nm was used in the following Examples. In the experiments, the average laser power at the focus of the objective was attenuated and adjusted by a variable attenuator, and was set below 160 mW (2 nJ pulse energy) to avoid gross optical damage in the hydrogel polymers. Three Newport VP-25xA linear servo stages with 100 nm resolution formed a 3D smooth scanning platform which was controlled and programmed by a computer. The focusing objective was a 60×0.70NA Olympus LUCPlanFLN long-working-distance objective which could precisely correct the spherical aberration and create nearly diffraction-limited laser focal spot at different depths below the material surface.

During the laser pulse irradiation sequence, the optical, hydrogel polymeric materials were maintained within an aqueous environment in a sandwich structure between two coverslips, and mounted horizontally on the scanning platform. The femtosecond laser pulses were focused vertically inside the hydrogel samples through the focusing objective. Different horizontal, constant scanning speeds from 0.4 μm/s to 4 mm/s were used with different polymeric hydrogels and different average laser power. A CCD camera was used to monitor the irradiation process and detect plasma illumination, which indicated the onset of laser-induced material breakdown. After laser irradiation, the materials were removed and observed under a calibrated Olympus BX51 microscope with different modes. The change in refractive index of the irradiated regions were measured either by grating experiments as described in L. Ding et al., "*Large refractive index change in silicone-based and non-silicone-based hydrogel polymers induced by femtosecond laser micro-machining*," Opt. Express 2006, 14, 11901-11909, or by a calibrated differential interference contrast (DIC) mode microscope.

Example 5A to 5D

Optical, hydrogel polymeric materials comprising hydroxyethyl methacrylate (HEMA), methylmethacrylate (MMA), ethylene glycol dimethacrylate (EGDMA) and variable concentrations of fluorescein-methacrylate (Fluo-MA), were prepared and are summarized in Table 1. A master monomer batch containing HEMA (83.7 wt. %), MMA (13.7 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 1. The monomer mixtures were polymerized according to well known methods in the art and cured in the form of 700 μm-thick flat films.

The HEMA-based hydrogel polymers have a water content of about 28% by weight and an average refractive index of 1.44. An Ocean Optics HR4000 spectrometer was usually used to measure their transmission spectra.

TABLE 1

| Ex. No. | 5A | 5B | 5C | 5D | 5E |
|---------|----|----|----|----|----|
| Fluor-MA | — | 0.0625 | 0.125 | 0.25 | 0.5 |

Figure 14:
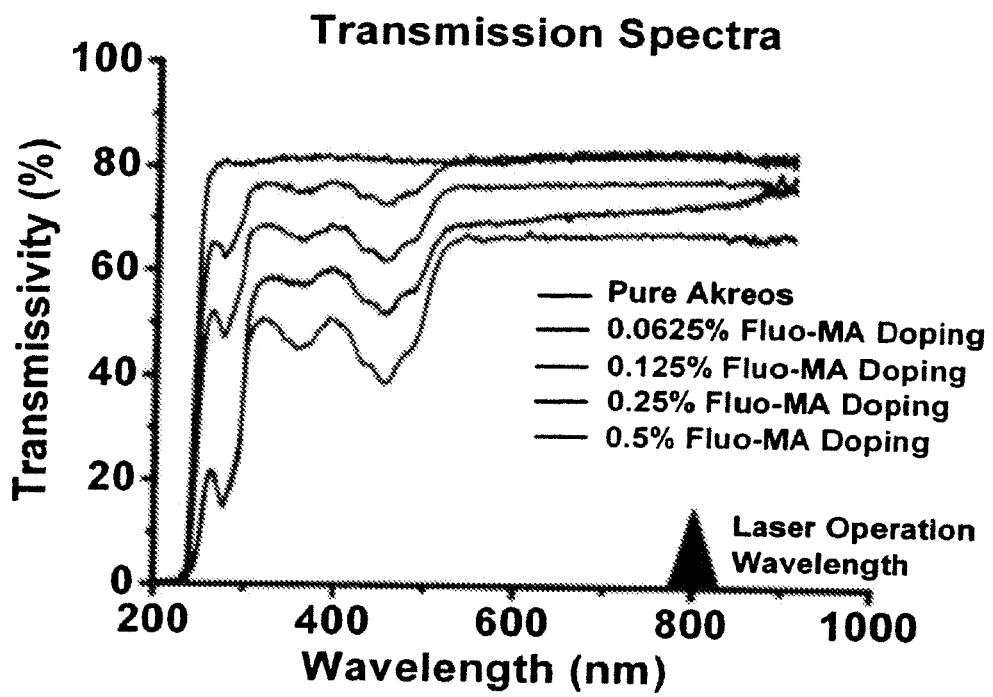
FIG. 14 are the transmission spectra of the hydrogel materials of Example 5.

FIG. 14 shows the transmission spectra of the non-photosensitized hydrogel material as well as the near identical hydrogel materials doped with different concentrations of Fluor-MA. As shown, the absorption peaks centered at about 350 nm to about 450 nm increased with an increase in the Fluor-MA concentration. Each of the Fluor-MA doped hydrogel materials remained transparent in the near infrared region though some scattering loss was observed at higher doping concentrations.

Figure 15:
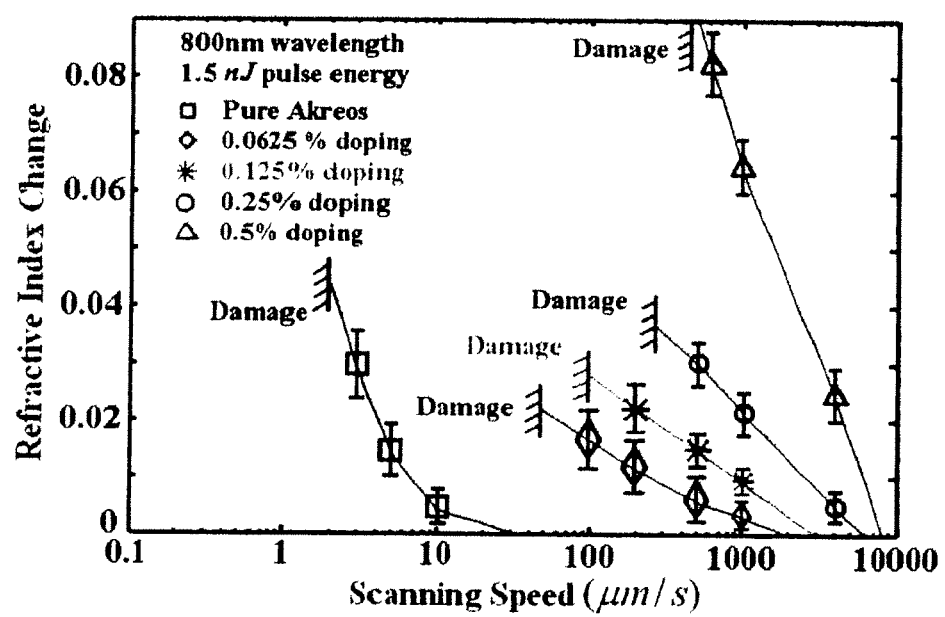
FIG. 15 is a plot of the measured change in refractive index at different scan rates for the hydrogel materials of Example 5.

Each of the HEMA-based hydrogel materials were micromachined (irradiated) with femtosecond pulse sequence at 800 nm and 120 mW average power. Horizontal periodic line arrays were typically written ~100-150 μm beneath the top surface of the materials at different constant scanning speeds. The changes in refractive index with different scanning speeds were measured for each material and are shown in FIG. 15. The degree of change in refractive index decreased as the constant scanning speed increased. For example, the largest refractive index change in the non-doped material was about 0.03±0.005 at a scan speed of 3 μm/s. Carbon damage spots were observed in the non-doped material if the scanning speed was less than 2 μm/s. Also, the degree of change in refractive index decreased very quickly as the scanning speed increased. At a constant scanning speed greater than 10 μm/s, the changes in refractive index were too small to be measured in our experiments (<0.005).

In contrast, with the doped hydrogel materials, we needed to significantly increase the scanning speed to avoid optical damage (carbonization) of the materials, which we believe is induced by accumulated heat. For Example 5B with 0.0625% Fluo-MA, a constant scanning speed of at least 40 μm/s was required to avoid carbonized damage to the material. For Example 5E with 0.5% Fluo-MA one would observe small spot evidence of damage within the material even at a scanning speed of 500 μm/s. Also, with irradiation of the Example 5E at a constant scanning speed of 600 μm/s, we measured a change in the refractive index of 0.085±0.005.

In general, the degree of change in the refractive index decreased as the Fluor-MA doping concentration decreased with a constant scan speed. For example, with a scanning speed of 1 mm/s, the measured change in refractive index for the 0.5% and 0.0625% Fluor-doped materials was 0.065±0.005 and 0.005±0.002, respectively. In fact, for the 0.5% Fluo-MA material, a change of refractive index of 0.025±0.005 was obtained at a scanning speed of 4 mm/s. These results indicate that nonlinear absorption within the hydrogel polymers could be greatly increased if Fluo-MA is copolymerized into the polymer network.

Large changes in refractive index could be observed at constant scanning speeds that are 1000× faster than for the non-doped material. If the Fluor-MA concentration in the hydrogel materials of Example 5 was too high, i.e., greater than 3 wt %, we began to see aggregates (scattering centers) form within the hydrogel polymer network. Accordingly, for the HEMA-based materials of Example 5, the Fluor-MA concentration is from about 0.05 wt. % to about 2 wt. %, or from 0.1 wt. % to about 1.5 wt. %. To summarize, we have shown that as the concentration of the photosensitizer monomer, Fluor-MA, in the polymeric hydrogels increased, we observed a corresponding increase in the degree of change in refractive index within the focal volume even at significantly greater constant scan rates (FIG. 15).

Figure 16A:
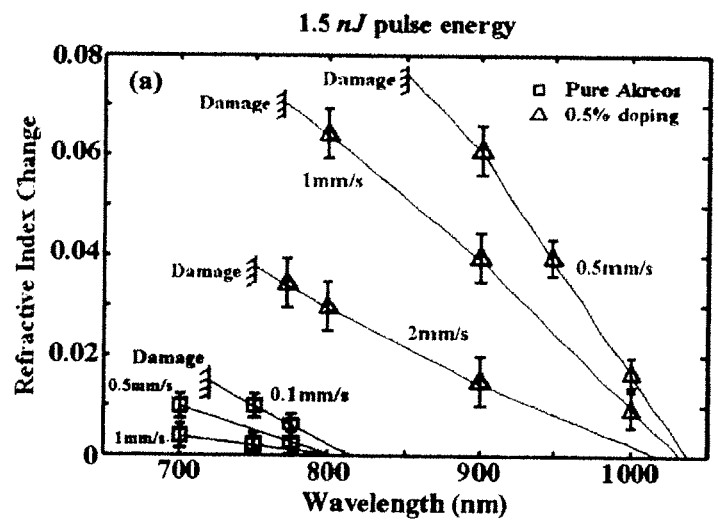
FIGS. 16A and 16B are plots of the measured change in refractive index at various wavelengths at average pulse energies of 1.5 nJ and 2 nJ, respectively, for the hydrogel materials of Examples 5A and 5E.
Figure 16B:
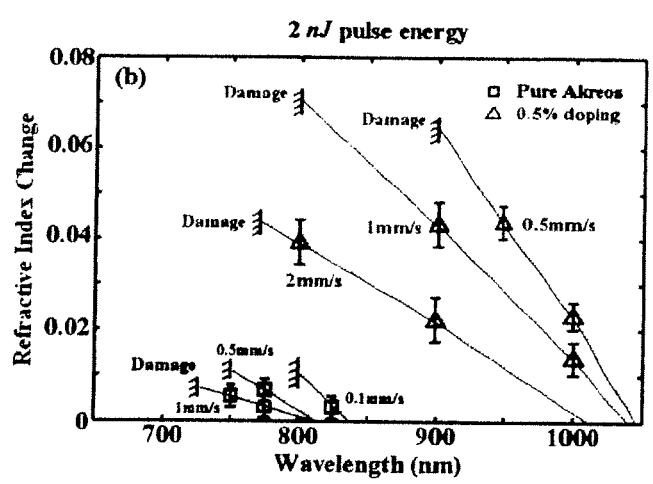

FIGS. 16A and 16B summarize our experimental investigations with Example 5A (non-doped) and Example 5E (0.5% Fluo-MA) using two different pulse energies: (a) 1.5 nJ (120 mW average power); and (b) 2 nJ (160 mW average power). For both hydrogel materials, the degree of change in refractive index decreased as the femtosecond laser was tuned to operate at a longer wavelength at a constant scan rate. For Example 5A, the degree of change in refractive index was less than 0.01 for all laser wavelengths. An attempt to increase the pulse energy or decrease the scan rate resulted only in optical damage. For all wavelengths longer than 850 nm, no change in refractive index was observed in Example 5A at either pulse energy even if the scan rate was greater than 100 μm/s. Higher pulse energies and slower scan rates were also tested in this wavelength region, but only optical damage with no change in refractive index was observed. In contrast, significantly large changes in refractive index were measured in Example 5E. In addition, because of the nonlinear absorption enhancement provided by the photosensitized material, material damage was observed at the shorter wavelengths. For example, even with a scan rate of 2 mm/s and a pulse energy of 1.5 nJ, some optical damage is observed at wavelengths less than 775 nm.

The irradiation of Example 5E at longer wavelengths (greater than 800 nm) did result in relatively large changes in refractive index within the focal volume of the material. FIG. 16A shows that one could achieve a change in refractive index of 0.06 in the focal volume of the material with a constant scan rate of 0.5 mm/s at a wavelength of 900 nm. Also, by increasing the average laser pulse energy from 1.5 nJ to 2.0 nJ, one could achieve even greater changes in refractive index, but some optical damage was observed. A comparison of the data and plots of FIG. 16A and FIG. 16B indicates that an increase in pulse energy from 1.5 nJ to 2 nJ results in optical damage at a wavelength of 900 nm and a scan rate of 0.5 mm/s. Also, if the scan rate is increased to 1 mm/s, we observed very small changes in refractive index (on the order of about 0.005).

Figure 17:
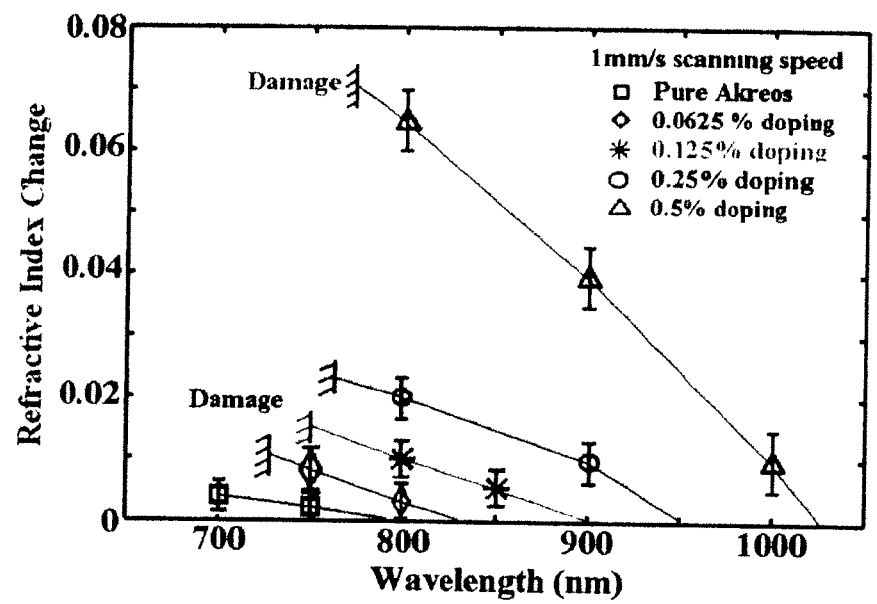
FIG. 17 is a plot of the measured change in refractive index at various wavelengths, an average pulse energy of 1.5 nJ and a scan rate of 1 mm/s for the hydrogel materials of Examples 5A and 5E.

To further investigate the wavelength dependence with respect to changes in refractive index within the focal volume, Examples 5A to 5E were irradiated over a wavelength range from 700 nm to 1000 nm at different scan rates and an average pulse energy of 1.5 nJ. For each hydrogel material, the degree of change in refractive index decreased with an increase in laser wavelength and increased with the Fluor-MA concentration. FIG. 17 shows the data and plots of Example 5E at a scan rate of 1 mm/s. The data of FIG. 17 is very helpful because it suggests a window of operating parameters in which one can form the refractive structures in the hydrogel materials, and yet, remain a safe working distance from causing any significant optical damage (scattering features) in the materials. For Example 5D and 5E, irradiation at 850 nm to 900 nm provides a safe working distance from optical damage, and yet provides a significant appreciable change in refractive index, i.e., from 0.01 to 0.04, at the given scan rate and average laser power—one can even see an appreciable change in refractive index at 950 nm for Example 5E.

As already stated, we believe that the presence of water within the polymer matrix, as in the case of a hydrated hydrogel material, plays a critical part in forming the observed changes in refractive index within the focal volume. Accordingly, we investigated the effect of water concentration on the degree of change in refractive index in the hydrogel materials of Examples 5B to 5E as well as those of similar composition, but with reduced water content. A master monomer batch containing HEMA (68.6 wt. %), MMA (28.9 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 2. The monomer mixtures were polymerized according to well known methods in the art and cured in the form of 700 μm-thick flat films. The hydrogel polymers of Example 6 have a 21% water content.

Likewise, the hydrogel materials of Example 7 were prepared from a master monomer batch containing HEMA (49.0 wt. %), MMA (48.4 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 2. The monomer mixtures were polymerized according to well known methods in the art and cured in the form of 700 μm-thick flat films. The hydrogel polymers of Example 7 have a 12% water content.

TABLE 2

| Ex. No. | 6A | 6B | 6C | 6D |
| --- | --- | --- | --- | --- |
| Fluor-MA | 0.0625 | 0.125 | 0.25 | 0.5 |

TABLE 3

| Ex. No. | 7A | 7B | 7C | 7D |
|---|---|---|---|---|
| Fluor-MA | 0.0625 | 0.125 | 0.25 | 0.5 |

Figure 18:
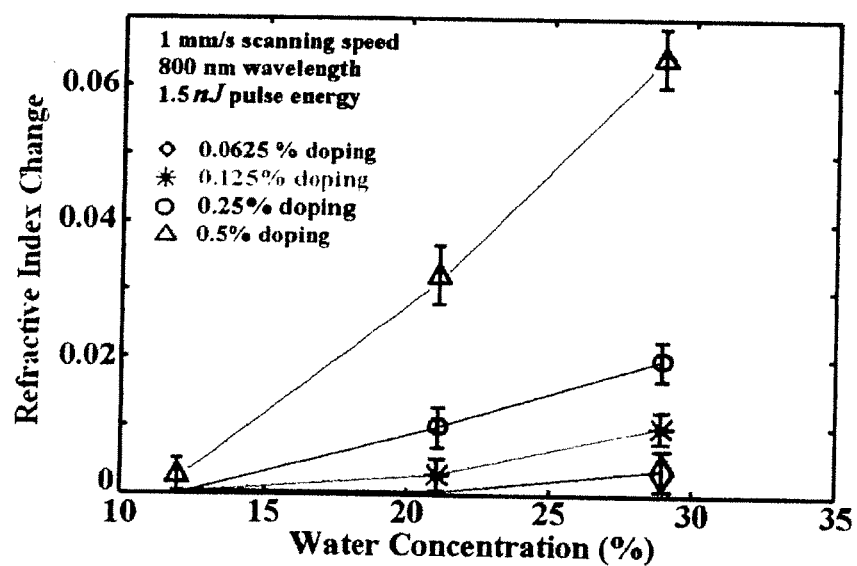
FIG. 18 is a plot of the measured change in refractive index for hydrogel materials with variable water content.

As indicated, each set of materials of Examples 5 to 7 have varying concentrations of the photosensitizer, Fluo-MA. FIG. 18 shows the resulting change in refractive index in these hydrogel materials at an irradiation wavelength of 800 nm, 1.5 nJ average pulse energy and a scan rate of 1 mm/s. As shown, the degree of change in refractive index decreased as the water concentration decreased in all the photosensitized hydrogel materials. We believe the localized water concentration of the hydrogel affects the thermodynamic properties such as specific heat, heat capacity, etc. as well as the material density of the materials. The largest change in refractive index is obtained in the hydrogels of Example 5, which have the largest water content of about 28%. Moreover, the hydrogels with relatively larger water content provide the largest safe working distance to form the refractive structures without optical damage to the material.

Figure 19:
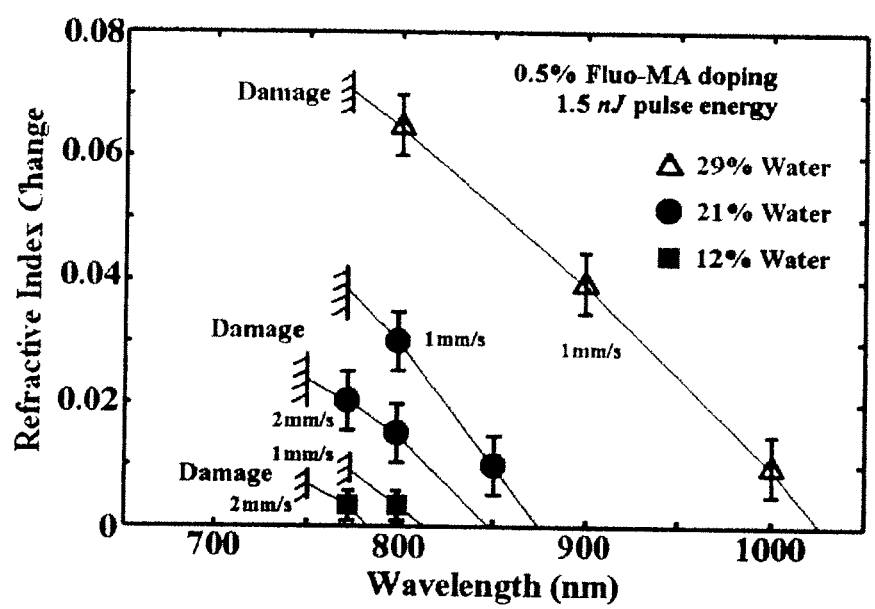
FIG. 19 is a plot of the measured change in refractive index at various wavelengths for hydrogel materials with variable water content.

We also investigated the wavelength dependence of the hydrogel materials of Example 5E, Example 6D and Example 7D, each with 0.5% Fluor-MA, but with the different water contents (see FIG. 19). A relatively large change in refractive index (greater than 0.02) without any optical damage was observed only in Example 5E at an average pulse energy of 1.5 nJ. One must note, however, that we also used a relatively fast scan rate of 1 mm/s in this investigation. As indicated, if the laser wavelength was less than about 750 nm, we observed only optical damage. If the laser pulses were operating at a wavelength greater than 800 nm, no change in refractive index is observed and optical damage is observed in the hydrogel materials of Example 7 (12% water content). For the hydrogel materials of Example 6 (21% water content), a change in refractive index of 0.01 is observed without optical damage if the irradiation wavelength is about 875 nm. Optical hydrogel materials that can be used in the process described is prepared from polymeric monomer formulations listed in Table 4.

TABLE 4

| Formulation | range (wt. %) | preferred range (wt. %) |
|---|---|---|
| hydrophilic component | 65 to 90 | 78 to 90 |
| alkyl(meth)acrylate component | 5 to 20 | 10 to 16 |
| aromatic component | 5 to 20 | 10 to 16 |
| crosslinker | 0.1 to 2.0 | 0.5 |
| photosensitizer | 0.4 to 4.0 | 1.0 to 2.5 |
| AIBN | 0.05 to 0.5 | 0.05 to 0.3 |

Optical hydrogel materials that can be used in the process described is prepared from polymeric monomer formulations listed in Table 5, and are listed as Example 8 and 9. Examples 8 and 9 was thermally cured as 1 mm thick films by very gradual ramped heating to a maximum temperature of 90° C. and subsequently sterilized by autoclaving. To obtain optically clear polymeric materials that were stable following the autoclaving of the materials it was necessary to include a solvent compatibilizer during the polymerization. Such solvent compatibilizers include polor organic solvents such as ethyl acetate or DMF. The amount of solvent compatibilizer varied between 7 wt. % to 20 wt. % based on the total weight of the monomeric components.

TABLE 5

| Example | 8 | 9 |
|---|---|---|
| HEMA | 84.5 | 83.6 |
| MMA | 13.8 | 13.7 |
| EGDMA | 0.5 | 0.5 |
| Monomer X | 1 | 2 |
| AIBN | 0.1 | 0.1 |

Monomer X is 2-[3'-tert-butyl-2'-hydroxy-5'-(3"-methacryloyloxypropoxy) phenyl]-5-chlorobenzotriazole:
HEMA is 2-hydroxyethyl methacrylate:
MMA is methyl methacrylate:
EGDMA is ethylene glycol dimethacrylate; and
AIBN is azobis(isobutyronitrile).

Refractive Structures with a Gradient Index

Without exclusion as to any lens materials or material modifications, e.g., the inclusion of a photosensitizer, or laser parameters described herein above, the foregoing disclosed techniques and apparatus can be used to modify the refractive properties, and thus, the dioptic power, of an optical polymeric material, typically, an optical hydrogel material, in the form of, but not limited to, an IOL or corneal inlay, by creating (or machining) a refractive structure with a gradient index in one, two or three dimensions of the optical material. The gradient refractive structure can be formed by continuously scanning a continuous stream of femtosecond laser pulses having a controlled focal volume in and along at least one continuous segment (scan line) in the optical material while varying the scan speed and/or the average laser power, which creates a gradient refractive index in the polymer along the segment. Accordingly, rather than creating discrete, individual, or even grouped or clustered, adjoining segments of refractive structures with a constant change in the index of refraction in the material, a gradient refractive index is created within the refractive structure, and thereby in the optical material, by continuously scanning a continuous stream of pulses. As will be described in greater detail below, since the refractive modification in the material arises from a multiphoton absorption process, a well controlled focal volume corrected for spherical (and other) aberrations will produce a segment having consistent and, if desired, constant depth over the length of the scan. As further noted, when a tightly focused laser beam consisting of femtosecond pulses at high repetition rate impinges on a material that is nominally transparent at the incident laser wavelength, there is little if any effect on the material away from the focal region. In the focal region, however, the intensity can exceed one terawatt per square centimeter, and the possibility of absorbing two or more photons simultaneously can become significant. In particular, the amount of two-photon absorption can be adjusted by doping or otherwise including in the irradiated material with selected chromophores that exhibit large two-photon absorption cross-section at the proper wavelength (e.g., between 750 nm and 1100 nm), which can significantly increase the scanning speed as already described. Also, multiple segments can be written into the material in a layer using different scan speeds and/or different average laser power levels for various segments to create a gradient index profile across the layer, i.e., transverse to the scan direction. Further, multiple, spaced gradient index (GRIN) layers can be written into the material along the z-direction (i.e., generally the light propagation direction through the material) to provide a desired refractive change in the material that corrects for some, most, or all higher order aberrations of a patient's eye.

To write refractive GRIN layers or structures in the materials, it can be advantageous to calibrate the effect of scanning speed and laser power against a measured change in the refractive index of the material within the focal volume. As an example, we prepared ten refractive structures in the form of diffraction gratings at different writing speeds while keeping all other parameters constant and measured the resulting diffraction efficiencies, and thereby determined the change in the refractive index of the material.

Figure 20:
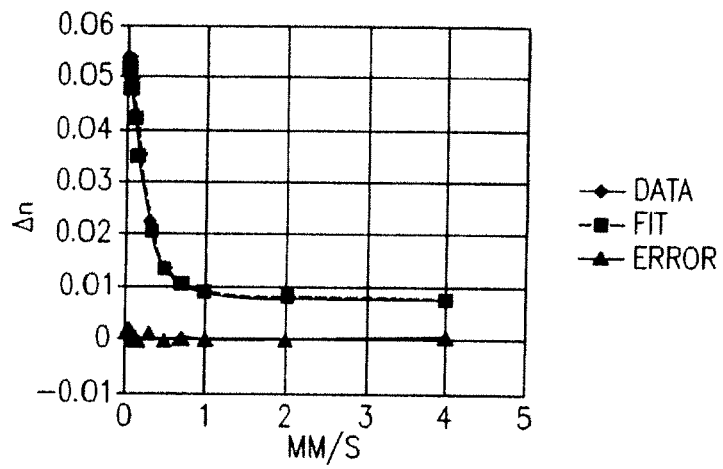
FIG. 20 is a graph showing change in index of refraction change (Δn) (vertical axis) vs. scanning speed (horizontal axis) for Akreos®-type hydrogel with 2% X-monomer in BBS at 370 mw average power at 800 nm with 100 fs laser pulses at 82 MHz repetition rate.

FIG. 20 shows the refractive index change in an Akreos®-like material as a function of the scanning speed in mm/sec for a given set of operating conditions: 400 mW average laser power, 100 fs pulse width, 800 nm wavelength, and focusing with a 0.7 NA air immersion microscope objective. FIG. 20 also shows an empirical fit to the data. Using this empirical fit, one can obtain the scan speed as a function of desired change in refractive index change simply by inverting the relationship. Then, by using the calibration curve shown in FIG. 20, one can write refractive structures that have a desired gradient index of refraction by changing the scanning speed. Alternatively, or in combination with changing the scanning speed, one can write refractive structures that have a desired gradient index by varying the laser (average) power.

Figure 21:
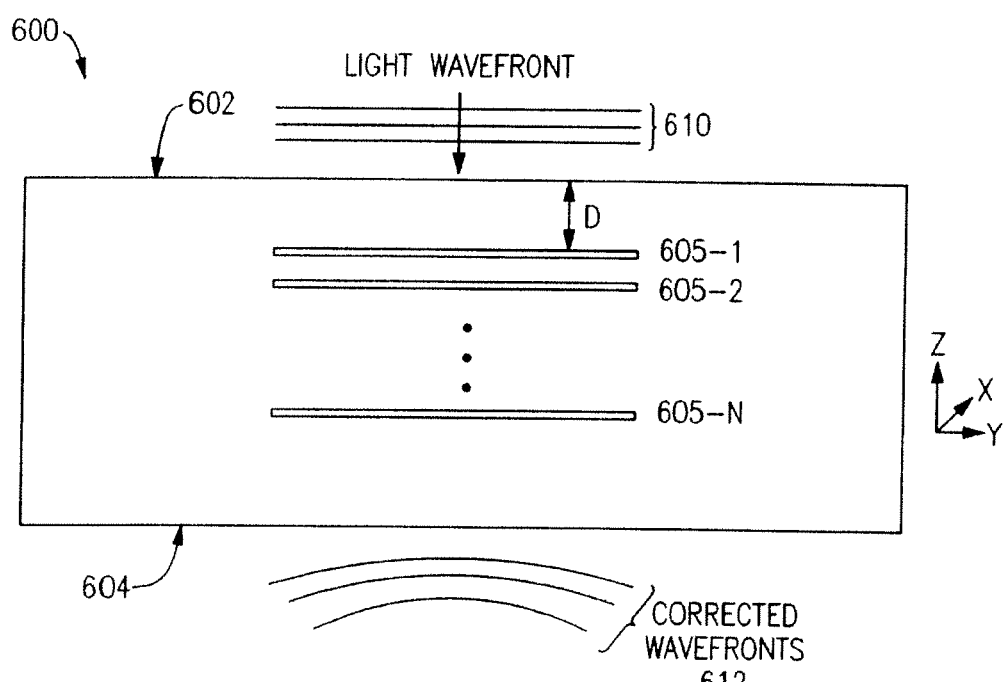
FIG. 21 shows a cross sectional schematic view of overlapping gradient index layers written into an optical polymeric material.

For ophthalmic applications, it is of particular interest that the GRIN refractive structures are low scattering (as discussed above) and are of high optical quality. FIG. 21 shows, in cross section, an ophthalmic hydrogel material 600 having an anterior surface 602 and a posterior surface 604 in which lateral GRIN layers 605-N with a thickness of 1 µm to 10 µm, and separated by a distance between layers (in z-direction), have been written in an optical polymeric material. As indicated, light 610 (shown in the form of waves) enters the optical material 600 through the anterior surface 602 and propagates through the material a distance D before contacting the first of the gradient index layer 605-1. Each gradient index layer 600-N comprises segments that can be written or formed as described above by scanning in the x direction or y direction. It is certainly to be understood by one of ordinary skill in the art that one can also scan in any direction within a defined xy plane (rotation about the z-axis) or at any angle from 45° to 135° to the z-axis. To maintain simplicity in the description, however, the gradient layers 600-N are shown at essentially 90° to the z-axis as well as the incoming light waves 610, and extend along, or are formed by scanning segments (i.e., line segments) along, the x-axis. Again, to maintain simplicity and for descriptive purposes only, the line segments along the scan direction are formed by maintaining a constant scan speed and constant average laser power along the scan direction. Accordingly, each line segment will provide a change in the index of refraction relative to the index of the material that is constant along the scan direction.

Following the writing of one line segment along the x-direction, an adjacent line segment is written. The adjacent line segment could be written using the same scan speed and laser power thereby providing an identical change in the index of refraction as the previously written line segment. Alternatively, the scan speed could be reduced with laser power unchanged resulting in a greater change in the index of refraction as compared to the previous written line segment. As stated, to make certain that there is little if no optical material between the adjacent segments that escapes index modification the spacing between adjacent segments is preferably less than the average line width of the two adjacent segments. This process of writing line segments is continued until the desired number of segments is written with the desired gradient index of refraction profile across the segments, i.e., across a dimension of the GRIN layer.

Lastly, as the light waves pass through the plurality of GRIN layers 605-N, the light waves bend with contribution from each GRIN layer and exit the posterior surface 604. The bending of the light waves provides a corrected wavefront 612, which provides a dioptic power change to the material, which in turn can be used to correct the vision of a patient.

Figure 22:
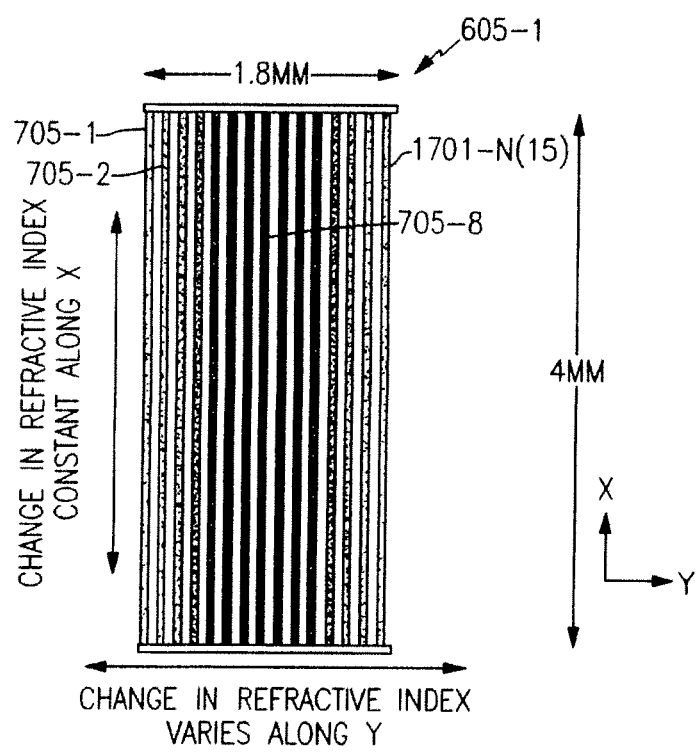
FIG. 22 shows a schematic view of multiple scan lines in a GRIN layer where each line is approximately two microns wide and the line spacing is one micron, according to an illustrative embodiment of the invention.

FIG. 22 is representative of a GRIN layer written within the optical material by the process just described with respect to FIG. 21. FIG. 22 is best described as a top view looking down upon the first gradient layer 605-1 of FIG. 21. As shown, GRIN layer 605-1 comprises a plurality N of line segments 705-1, 705-2, 705-3, ..., 705-N that are substantially parallel and each line segment having a line width of between about one to five µm (e.g., 2 µm, 3 µm, or 4 µm) and an intersegment spacing that is less than the segment line width (for segments of approximately equal line width, as shown), or for variable segment widths of two adjacent scan segments, the intersegment spacing is less than an average line width of the two adjacent scan segments. In reference to FIG. 21, the segments are formed by scanning 4 mm along the x-direction, each segment written with a constant change in refractive index along the scan direction. It is noted that for descriptive purposes only, the segments are numbered 705-1, 705-2, 705-3, ..., 705-N, but each representative line segment is actually a collection of several hundred line segments that have been written into the material. This is well understood by persons of skill in the art because one immediately recognizes that the depicted fifteen segments, each having a line width and intersegment spacing, for example, of 5 µm and 4 µm, respectively, would only cover a distance in y of about 60 µm, whereas the actual structure formed extends about 1.8 mm in the y direction. Accordingly, the actual number of segments written is close to 4500 total segments (each depicted segment representing about 300 written segments). Also, the white line segments depicted between each segment are present only to distinguish the writing of each respective segment. In actuality, there is little or no spacing of non-index modified material between segments. In particular, beginning from the far left of gradient layer 605-1 each adjacent segment is written as one moves laterally in the y-direction. In this one example, a total of fifteen (15) segments are represented or depicted until a desired width of the gradient layer is achieved. As shown, gradient layer 605-1 has a width of 1.8 mm, and comprises a gradient index change along the y-direction and a constant index change along the x-direction.

As indicated, gradient index layer 605-1 includes a parabolic gradient index profile with the change in the index of refraction increasing as one moves left in the y-direction from segment 705-1 to 705-8. Again, there are at least two ways one can provide an increase in the change of index across segments: one, to reduce the scan speed of respective segments as one moves along y, or to increase average laser power of respective segments as one moves along y. Of course, one of ordinary skill can use other irradiation or optical conditions to achieve a similar result. Once segment 705-8 is completed, the scan speed is increased, or the average laser power decreased for segment 705-9, thereby setting a trend of a decrease in the change of index as one continues to move along in the y-direction until segment 705-15 is written.

Figure 23A:
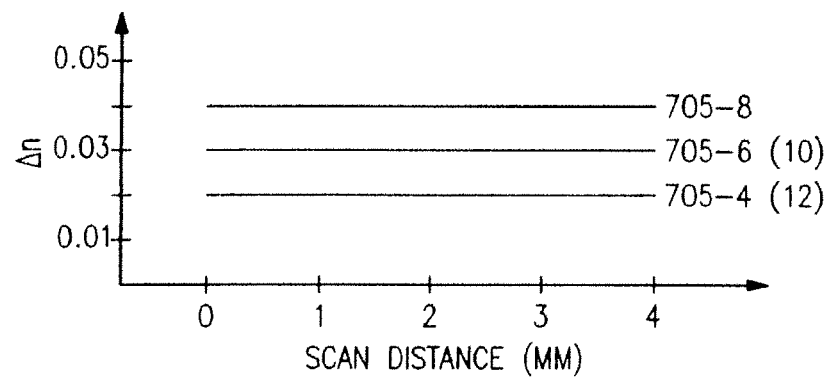
FIG. 23A is a graphical representation of gradient index profiles of selected scan segments along the x-axis of GRIN layer 605-1 of FIG. 22.
Figure 23B:
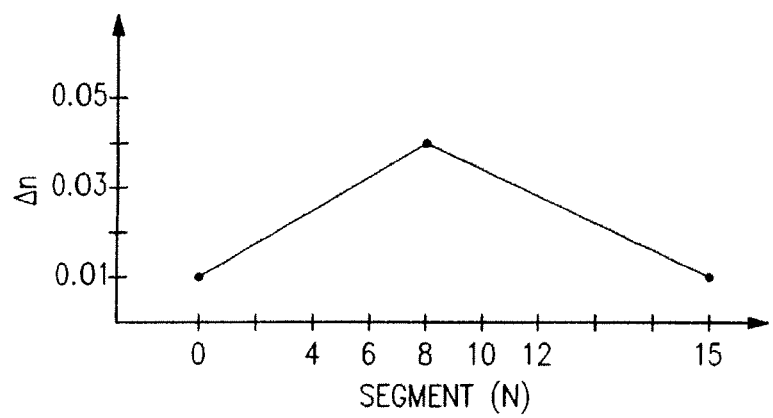
FIG. 23B is a graphical representation of a gradient index profile of GRIN layer 605-1 along the y-axis of FIG. 22.

FIGS. 23A and 23B is a graphical representation of a gradient index profile of GRIN layer 605-1 of FIG. 22. FIG. 23A is a graphical representation of the change of index of refraction for selected segments 705-N of gradient layer 605-1. The stated change in the index of refraction is in relation to the index of refraction of the optical material outside the focal volume. As indicated, segments 705-4 and corresponding segment 705-12 are written with a selected scan speed and average laser power to provide a change in the index of refraction of the material of 0.02 along the entire segment length. Likewise, segments 705-6 and corresponding segment 705-10 are written with a selected scan speed and average laser power to provide a change in the index of refraction of the material of 0.03. Segment 705-8 is written with a selected scan speed and average laser power to provide a change in the index of refraction of the material of 0.04. FIG. 23B is a graphical representation of the gradient index profile along the y-axis of gradient layer 605-1. Although FIG. 23B is depicted as a smooth continuous curve in the y-direction, one of ordinary skill in the art would understand that there is likely to exist some variation or jaggedness in an actual gradient profile due in-part to the process described and the dimensions involved with the focal volume and the ability to accurately set scan coordinates of the laser system.

Figure 24:
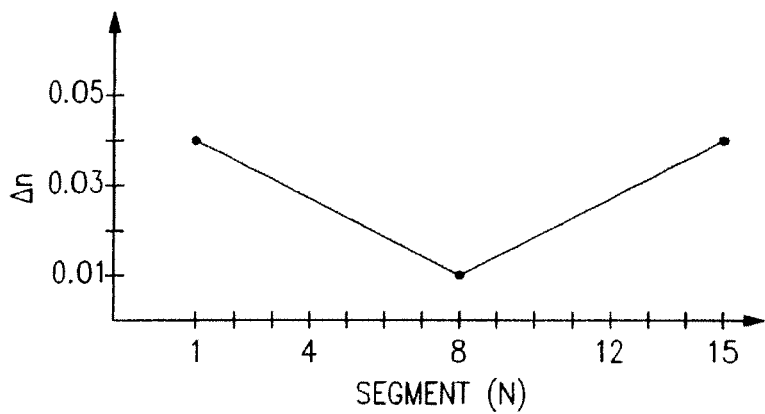
FIG. 24 is a graphical representation of a gradient index profile of a GRIN layer along an axis transverse to the scan direction that could be used to provide a negative dioptic power correction to an optical polymeric material.

It is also understood by those of ordinary skill that the gradient index profile along the y-direction can have any preselected shape. Whereas the gradient profile depicted in FIG. 23B will have an effect of a positive lens element one can just as easily prepare one or more gradient index layers with an inverted gradient profile, thereby providing an effect of a negative lens element, FIG. 24.

Figure 25A:
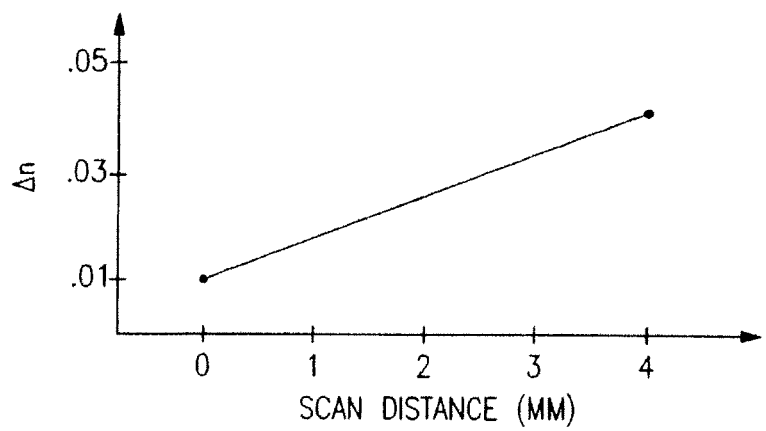
FIG. 25A is a graphical representation of a gradient index profile of a segment of a GRIN layer as the segment is written.
Figure 25B:
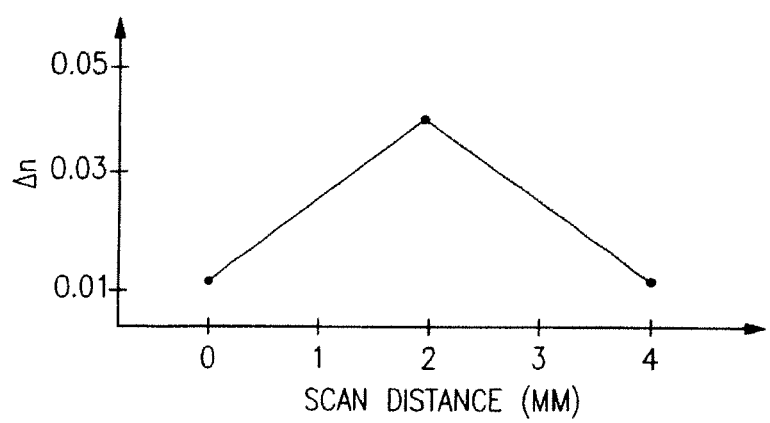
FIG. 25B is a graphical representation of another gradient index profile of a segment of a GRIN layer as the segment is written.
Figure 25C:
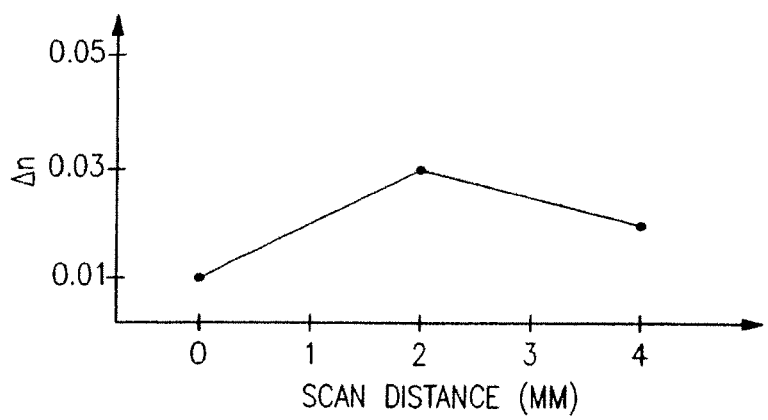
FIG. 25C is a graphical representation of another gradient index profile of a segment of a GRIN layer as the segment is written.

In addition to, or as an alternative to, the gradient index profile being written along the y-direction, one can also write a gradient index layer along the scan direction. FIGS. 25A to 25C exemplify some preferred gradient index profiles of a gradient layer along the scan direction. As stated, such a gradient layer can be formed by modulating laser power, or varying scan speed, during the scan, i.e., as each segment is being written. FIG. 25A exemplifies how the change in refractive index of the material can increase at substantially a constant rate along the entire scan direction. Likewise, one of ordinary skill can also envision how the change in refractive index of the material can decrease at substantially a constant rate along the entire scan direction (not shown). FIG. 25B exemplifies how the change in refractive index of the material can increase at substantially a constant rate along half the scan direction to the midpoint of the segment, and then decrease at a substantially a constant rate to the end of the segment. Likewise, one of ordinary skill can also envision how the change in refractive index of the material can decrease at substantially a constant rate along half the scan direction to the midpoint of the segment, and then increase at a substantially a constant rate to the end of the segment (not shown). FIG. 25C exemplifies how the change in refractive index of the material can increase at substantially a constant rate to some transition point along the scan direction, and then decrease at the same rate to the end of the segment. Likewise, one of ordinary skill can also envision how the change in refractive index of the material can decrease at substantially a constant rate to some transition point along the scan direction, and then increase at the same rate to the end of the segment (not shown). The described gradient index profiles are provided for descriptive purpose only, and one of ordinary skill in the art can certainly envision any number of gradient index profiles. For example, it is well understood by those in the art that a change in refractive index of the material along a segment can be constant, or increase or decrease step wise or continuously along the segment at more than one rate of change.

Figure 26A:
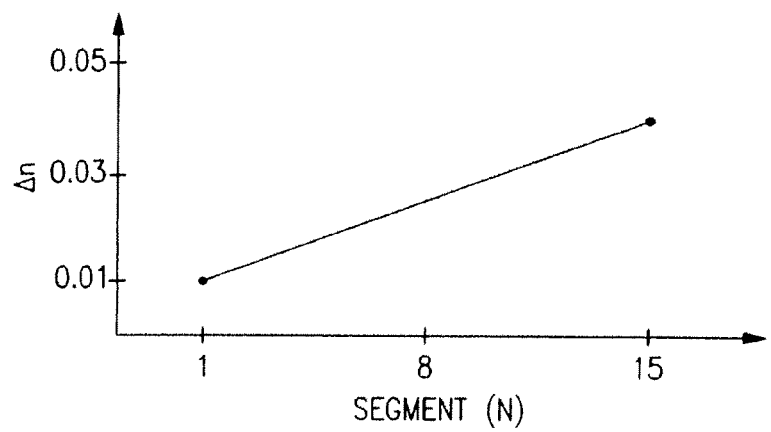
FIG. 26 A is graphical representation of a gradient index profile of a GRIN layer along an axis transverse to the scan direction.
Figure 26B:
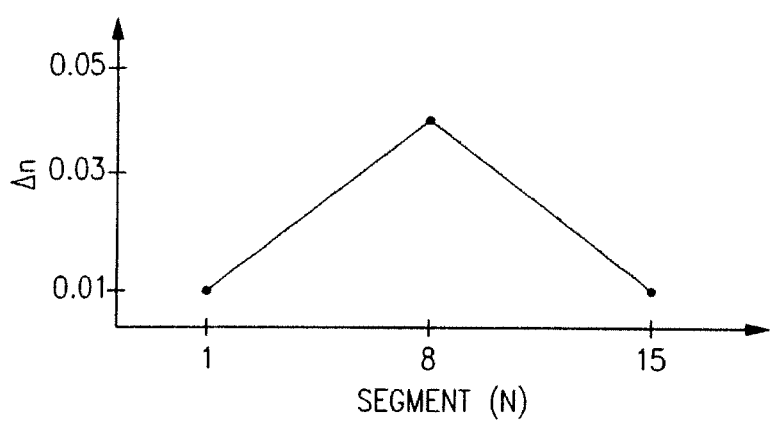
Figure 26C:
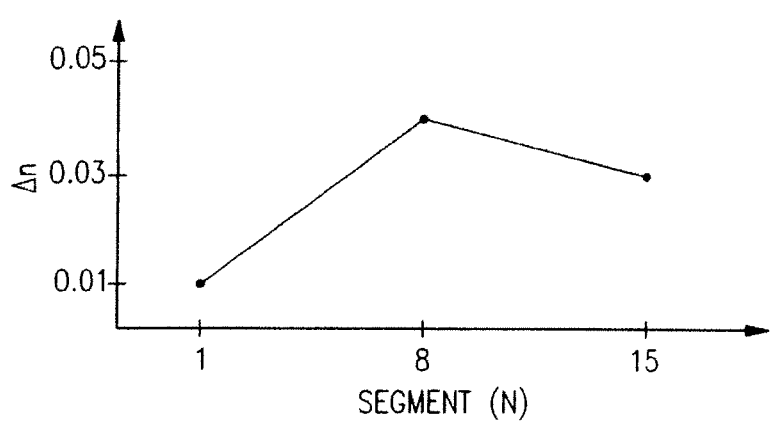

For every exemplary gradient index profile described above along the scan direction, a similar gradient index profile of the one or more gradient index layers can be achieved by varying the change of the index of refraction across or between at least five or more adjacent segments (e.g., 5 to 1000 segments) of a GRIN layer, at least thirty or more adjacent segments (e.g., 30 to 1000 segments), at least one hundred or more adjacent segments (e.g., 100 to 1000 segments). FIGS. 26A to 26C exemplify some preferred gradient index profiles of a gradient layer across different segments, i.e., essentially transverse to the scan direction. As stated, such a gradient layer can be formed by modulating laser power, or varying scan speed in regions of adjacent segments. FIG. 26A exemplifies how the change in refractive index of the material can increase at substantially a constant rate along a series of adjacent segments. Likewise, one of ordinary skill can also envision how the change in refractive index of the material can decrease at substantially a constant rate along a series of adjacent segments (not shown). FIG. 26B exemplifies how the change in refractive index of the material can increase at substantially a constant rate along a first region of adjacent segments, and then proceed to decrease at a substantially a constant rate along a second region of adjacent segments. Likewise, one of ordinary skill can also envision how the change in refractive index of the material can decrease at substantially a constant rate along a first region of adjacent segments, and then proceed to increase at a substantially a constant rate along a second region of adjacent segments (not shown). FIG. 25C exemplifies how the change in refractive index of the material can increase at substantially a constant rate along a first region of adjacent segments, and then proceed to decrease at a different rate along a second region of adjacent segments.

FIGS. 26A to 26C exemplify some gradient index profiles of the gradient index layers transverse to the scan direction. By no means are the gradient profiles limited to these shapes. For example, it is well understood by those in the art that a change in refractive index of the material across a plurality of segments can be constant, or increase or decrease step wise or continuously along the segment at more than one rate of change.

When writing gradient index microstructures in ophthalmic devices, under some conditions the accumulated phase difference in some regions of the structure may exceed $2\pi$. In those regions, the design of the gradient index structure can be modified to provide a phase shift that is modulo-$2\pi$. In other words, in the regions where the phase shift is between $2\pi$ and $4\pi$, a constant phase shift of $2\pi$ can be subtracted from the total phase shift. Similarly, if the phase shift according to the design would place the phase shift in the range $4\pi$ to $6\pi$, then a constant $4\pi$ phase shift can be subtracted from the design in that region. This process for accounting for the phase shift can be advantageous in some cases in helping to reduce the total device writing times.

As stated, change in the index of refraction will vary within each gradient index layer in a prescribed manner according to the desired functional requirements of the device. For instance, if a focusing lens is desired, it will be advantageous to have the change in the index of refraction vary quadratically. If the maximum index change is in the center and the change decreases outward to the edges, then the structure will provide focusing power. In the reverse case, where the index change is maximum at the edges and decreases toward the center, such a structure will provide divergence, or negative focusing power. Furthermore, if one or more layers 605 are written with a quadratic index change of a given magnitude and orientation (e.g., x-direction) and one or more different layers are written with a quadratic index change of different magnitude and orientation (e.g., y-direction), an astigmatic crossed-cylindrical lens structure results, which is applicable for vision correction in intraocular lenses. Refractive segments can also be written as concentric segments radiating outwardly from a central location, or as arcuate or curved segments. Also, the refractive segment can be written as a planar layer (of relatively constant thickness), or the refractive segment can vary in the z-direction, i.e., vary in thickness.

In an illustrative aspect, we wrote a cylindrical lens structure with a one-dimensional quadratic gradient index structure as shown in FIG. 21 with three GRIN layers each 5 μm thick as illustrated in FIG. 22, spaced by 10 μm (z-direction). Accordingly, there exists a layer of non-modified optical material having a thickness of about 5 μm to 7 μm between each GRIN layer. The resulting cylindrical lens was designed to provide approximately 1 diopter of astigmatism uniform along the length of the device.

Figure 27B:
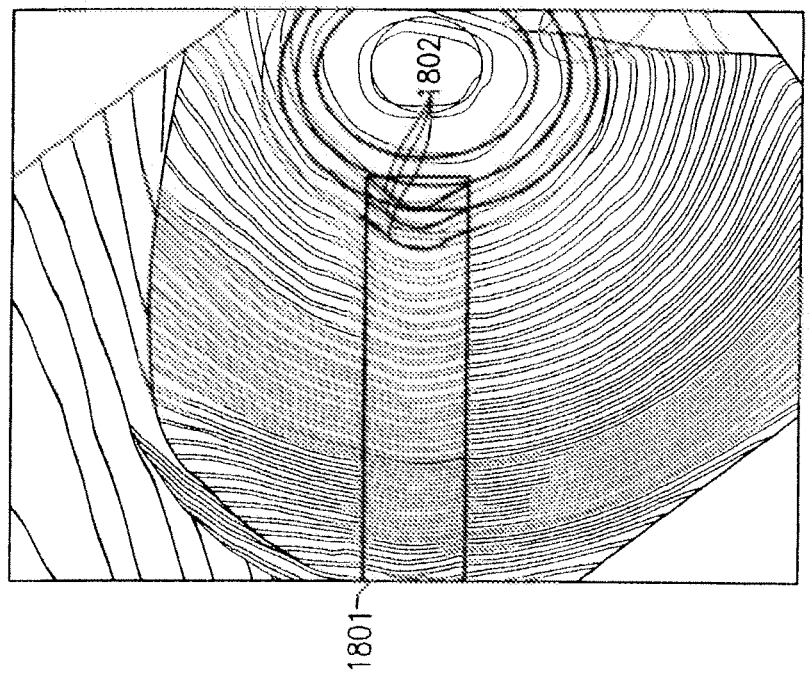
FIG. 27B is a schematic representation of the Twyman Green interferogram of FIG. 27A.
Figure 27A:
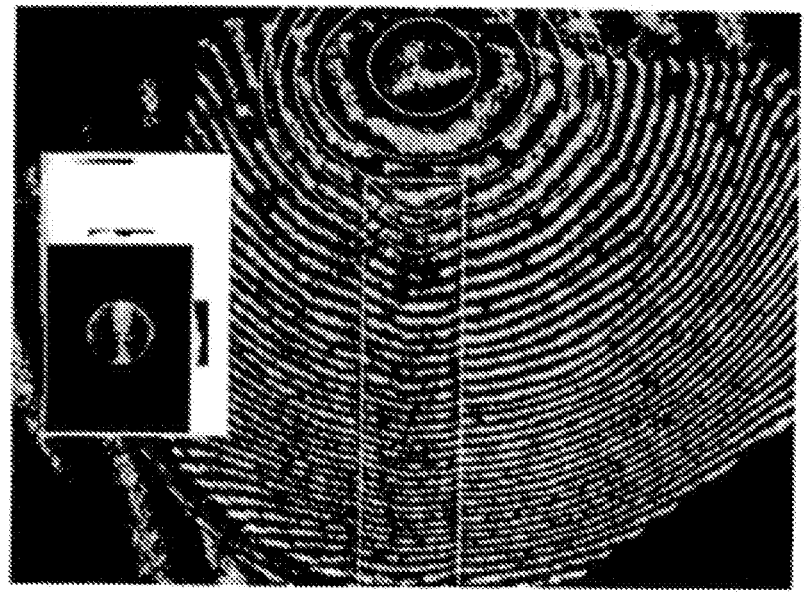
FIG. 27A shows a Twyman Green interferogram of a one dimensional quadratic gradient index device that is 1.8 mm wide by 4 mm long (rectangle) written in Akreos:X monomer (curved line segments show quadratic phasefronts), according to an illustrative embodiment of the invention.

FIG. 27 shows a Twyman Green interferometer image (FIG. 27B is a schematic representation of FIG. 27) of the lens structure 1801 (rectangular region) showing nominally quadratic phase contours 1802 in the lens area. The inset shows a phase topography measurement that confirms the parabolic nature of the phase readings. Imperfections in the xyz high speed piezoelectric translation stage and scanning procedure cause localized index fluctuations that result in random phase shifts, but the general appearance of the fringes is as expected. One can speculate that the observed phase shifts is caused by a nonuniformity in the scanning process, either in the scanning speed or in the line spacing. Furthermore, the 3D high speed ultrasonic piezoelectric stages that we used (PolyTek PI) exhibited some retracing errors wherein the return scan line was located a few microns below the height of the initially scanned line, which could have caused some random phase errors. The measured astigmatism (corrected for any baseline astigmatism in the glass and hydrogel substrate) varied between +0.3 and +0.9 diopters along the length of the sample.

Refractive structures having a gradient index are highly versatile, and can be written, as described, as vertically spaced (z-direction) layers with each GRIN layer being different in order to achieve different results. For hydrogel materials, e.g., in order to maintain high index change, it is advantageous to maintain a spacing between the GRIN layers in the range of 5 μm to 10 μm or so. For example, in order to keep the devices compact, it is desirable to minimize the spacing between the GRIN layers, e.g., a spacing of 5 μm, 6 μm, 7 μm, 8 μm, or 9 μm.

It is desirable to be able to correct not only sphere and cylinder in vision correction, but also higher-order aberrations. It is also desirable to provide advanced designs that can provide multi-focal effects in order to alleviate symptoms of presbyopia. Furthermore, it is desirable to minimize the effects of "rainbow," which is a diffraction-based effect, in which diffracted peaks are seen at angles $m\lambda = d \sin \theta$ where m is the diffraction order, $\lambda$ is the wavelength of interest, and d is the grating period. This effect is expected when the line spacing is larger than the wavelength of light being used for observation. For example, in our development of the described GRIN refractive structures adjacent segments with intersegment spacing that exceeded the average segment line width of the adjacent segments exhibited visible coloration or a rainbow effect, however by decreasing the intersegment spacing to less than the average segment line width of the adjacent segments, e.g., 0.8 μm to 0.5 μm for an average segment line width of 1 μm, the observed "rainbow" effect is significantly reduced. With the intersegment spacing of the adjacent segments less than the average segment line width of the adjacent segments there is by necessity some overlap in focal volumes of the adjacent segments. Accordingly, it is important to minimize any material damage that can result from irradiating volumes of material more than once because we know that material damage will cause light scattering.

In addition to the use of known adaptive optics systems and techniques, precise control of short light pulses from a laser to form refractive segment(s) or gradient index layer(s) that can be written into an IOL at a depth of five mm (or more) from the front surface of a patient's cornea and into the IOL is described. High (nearly diffraction-limited) focus is maintained by an adaptive optic element with real-time feedback during scanning operations using an active feedback that is provided by a two-photon fluorescence signal.

It is known that high numerical aperture (NA>0.7) microscope objectives effectively used for writing refractive index modifications in a polymer material have a maximum working depth of about 3.2 mm. It is further appreciated that an implanted IOL may be located at a depth of 5 mm or more behind the anterior corneal surface. Furthermore, aberrations induced at the corneal surface severely degrade the focused beam quality. The use of water immersion objectives provides increased focusing quality, but still with limited depth resolution. Also, the use of water immersion generally requires applanation of the corneal surface during surgery. In addition, in order to write refractive corrections inside the IOL, it will be preferred to scan regions of the cornea that are significantly off-axis, which will introduce large higher order aberrations and degrade the focused beam quality.

These recognized problems have encouraged a solution in the form of a method and apparatus that can achieve diffraction-limited focusing with air immersion using a long working distance (e.g., up to 12 mm), high NA (i.e., >0.5) objective integrated with a scanning system that provides real-time control of the focus and maintains it during the scanning or writing process.

Figure 28:
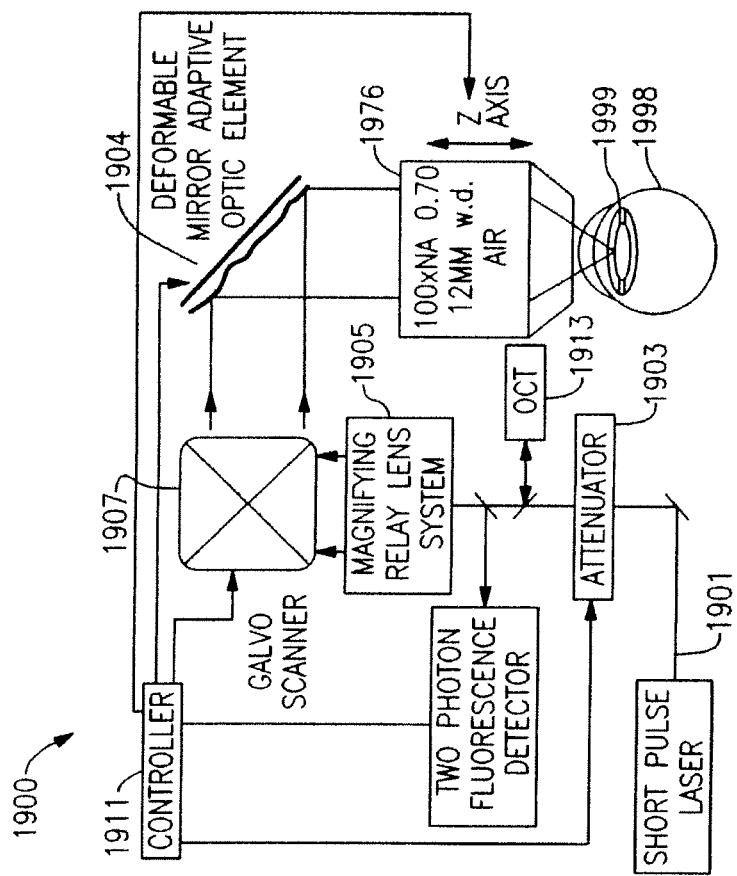
FIG. 28 shows a schematic view of an adaptive optic galvo-scanning system with real-time focusing feedback, according to an illustrative embodiment of the invention.

According to a non-limiting exemplary embodiment, an adaptive optic scanning system 1900 with real-time feedback is schematically illustrated in FIG. 28. A short pulse laser beam 1901 passes through a computer controlled beam attenuator 1903 to set the desired laser power. The beam then passes through a magnifying relay telescope 1905 that is designed to optimally fill the input pupil of a microscope objective 1976. The magnification and design of the relay lens system also is set to image a two dimensional galvanometer scanner 1907 into the input pupil of the microscope objective. The two-dimensional galvanometer scanner can provide high speed re-targeting of the beam typically in about 20 microseconds. After the galvanometer, the beam is reflected from a deformable mirror 1904, which is controlled by a computer and changes shape in response to signals from controller 1911. The light is focused into the eye 1998 and into the interior of an implanted IOL 1999 using a long working distance product inspection objective that has a 100×NA 0.70 specification with a working distance of 10-12 mm (such as Mitutoyo M PLAN NIR HR BF 100×NA 0.70, WD 10.0 mm or M PLAN NIR BF 100×NA 0.50, WD 12.0 mm). The Z-axis or focusing dimension is controlled with a Z-axis scanner (not shown) that is attached to the microscope objective, whereas the X-Y scanning is provided by the galvanometer system. Additional scanning components may be included that provide scanning of the patient's head or, alternatively, scanning of the adaptive optic with the focusing lens.

In one optic system embodiment, an epi-mode (back-detected), exogenous or endogenous (from a two-photon chromophore that is used as a two-photon enhancer in the IOL) two-photon fluorescence signal is used as a detector of the focus quality For example, a wavefront aberration test is initially conducted on a patient to determine the number and type of refractive structures, preferably, the GRIN structures described, that are to be written into an IOL. Once the patient is appropriately positioned, a preliminary scan is done with the OCT (optical coherence tomography) system 1913 to locate the interfaces of the IOL. The laser is then operated at low power (~5 mw) and the two-photon fluorescence signals are detected. The two-photon fluorescence signal at each of a defined grid of points is optimized such that the two-photon signal is optimized at each scan point in the aberration correction grid. At each point, the optimum settings of the deformable mirror can be determined that give the highest two-photon fluorescence signal. The settings are then saved for the scanning or writing process. The laser is power is then increased and the scanning or writing of the refractive structures commences. At each galvo-scanning point, the deformable mirror returns to the wavefront correction setting that provided the optimum focusing and the highest two-photon fluorescence signal, thereby providing nearly diffraction-limited focusing throughout the scan region.

The aberration correction grid does not have to be as fine as the micromachining grid, but should be fine enough so that the aberrations are corrected on a fine enough scale so that the focusing is maintained at nearly diffraction-limit throughout the scanning process. For example, a rough correction grid could be used in combination with an interpolation routine, and the aberration correction could be interpolated inside the grid points for higher efficiency.

One must also consider to compensate for the optical aberrations that result when writing deep into a material. The use of a NA 0.7 microscope objective provides optimum experimental results in terms of dynamic range (the range of index of refraction changes that can be obtained above baseline and before damage sets in). At such a high NA, it is necessary to fully compensate the relevant aberrations, most importantly spherical aberration.

Discussion of Gradient Index (GRIN) Layers

Figure 29:
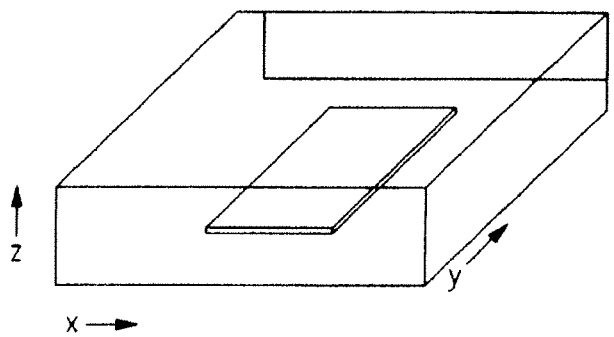
FIG. 29 shows a schematic view of a single layer gradient index structure written in an optical polymeric material, according to an illustrative aspect of the invention.

An xyz translation system can be used to write gradient index (GRIN) layers. The thin (1-10 µm) layers cause a variable phase shift in the plane, resulting in a curvature of the phase fronts of the light. FIG. 29 shows a three-dimensional representation of a single, thin GRIN layer written into a flat piece of polymer material. As already discussed there are several modes in which the refractive structures can be written. Since the gradient index of refraction change depends on the variation in scan speed and/or the optical power, we can write refractive devices using either mode, or both together. We refer to these herein as "speed mode" and "power mode" for convenience.

1) In 1D Speed Mode, to write a single, thin GRIN layer, the translator is first set to the required z-position to set the height of the layer inside the material. The translator is scanned along the y-direction at a speed that is uniform along y, and varies along x for one or more written segments. For instance, the speeds can be programmed to produce a parabolic index change. This will produce a cylindrical lens with refracting power in the x-direction that is uniform in the y-direction. In 2D Speed Mode, the translator is scanned along the y-direction at a non-uniform speed such that the index change is non-uniform along the y-direction. The non-uniform y-speed can also be changed along the x-direction, resulting in a two-dimensional gradient index layer.

2) In 1D Power mode, to write a single, thin GRIN layer, the translator is first set to the required z-position to set the height of the layer inside the material. The translator is scanned along the y-direction at a uniform speed and the intensity of the femtosecond laser pulses is set to a different average power by a light modulator such as an acousto-optic or electro-optic modulator for each y-scan. As a result, the index change is different for each x-position. For instance, the intensities may be set to produce a quadratic index variation along the x-direction. In 2D Power Mode, the light intensity is varied continuously along the y-scan during the y-scan, and the light intensities can varied for each x-position. This results in a two-dimensional gradient index layer.

Figure 30:
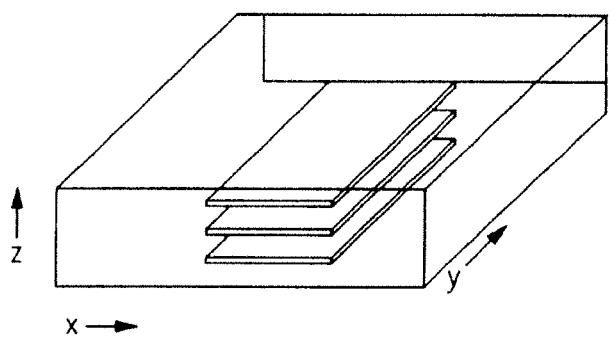
FIG. 30 shows a schematic view of a three layer gradient index structure written in an optical polymeric material, according to an illustrative aspect of the invention.

Either of these techniques can be repeated, and after each layer is written along the z-axis, the GRIN layers are spaced or separated by 5 to 10 microns, e.g., 6 microns, 7 microns, 8 microns or 9 microns. FIG. 30 shows depicts three GRIN layers written into an optical polymeric material. Each individual GRIN layer can have the same or different gradient index profile as the GRIN layer below or above. For instance, one layer may have the index gradient in the x-direction and another layer may have the index gradient in the y-direction. This would result in a "crossed cylinder" optical approach, which is similar to a spherical lens, except that it can offer certain design degrees of freedom.

3) Combined Speed and Power mode. In some cases, it may be advantageous to combine the speed and power modes. For instance, power mode could be used to vary the index change along the y-direction, and the scan speeds could be varied along the x-direction, and/or the reverse.

Figure 31B:
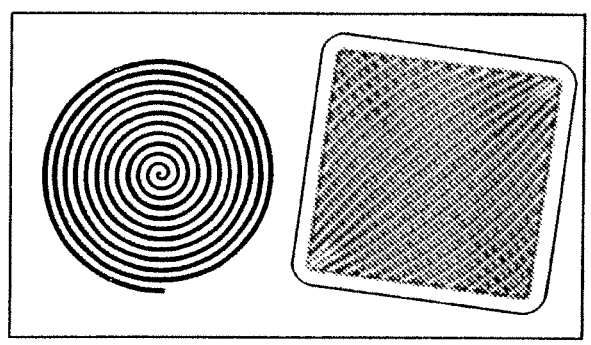
FIG. 31B is a schematic representation of the GRIN layer of FIG. 31A.
Figure 31A:
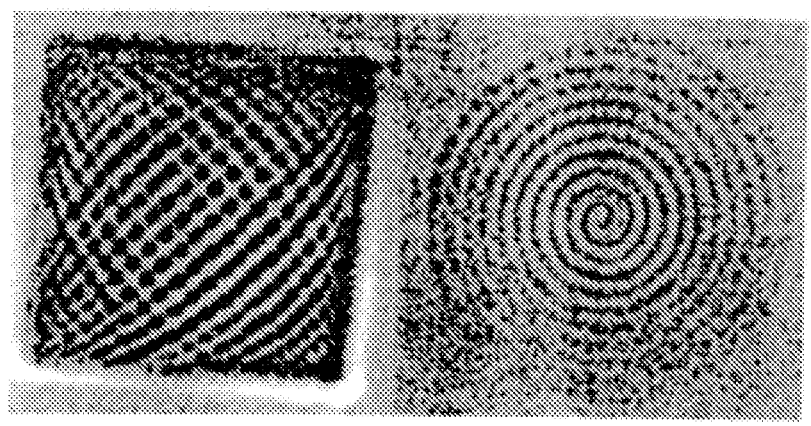
FIG. 31A shows two-dimensional, single GRIN layer written in Thiol-ene:ITX with a galvo controlled system, according to an illustrative aspect of the invention.

4) Galvanometer controlled systems. In the case of scanning systems that rely upon galvanometer-type control systems, it is possible to address different points in the sample at high speeds in arbitrary patterns, resulting in complex gradient index possibilities. In this case, the localized index changes will depend on the laser power modulation and the local scanning speed. Using a two dimensional galvo system with a custom designed optical relay lens system, we were able to write two dimensional, gradient index refractive structures in Thiol-ene type optical materials doped with ITX. FIG. 31 shows some preliminary results obtained by driving the galvanometers in out-of phase repetitive patterns. These are commonly referred to as Lissajous patterns. It is possible to write two-dimensional gradient index patterns with radially symmetric index gradient using such a system, and the control system for such a writing procedure could use a combination of variable scan speed control and optical power control as discussed previously for the case of xyz scanning.

Typically, galvo-controlled systems designed for high NA focusing are limited to scanning over a small area (e.g., 350-450 µm diameter) as a result of their short effective focal length. In order to write relatively large refractive structures, a high NA large field optical system is likely to be necessary. One can also stack the scanning systems, for example, one can use a combination of galvo-scanning and sample translation. Planar gradient index structures such as those shown in FIG. 31 can be written in multiple layers also as shown in FIG. 31, and again, the gradient index profiles of each layer could be the sameor different.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the invention described herein without departing from the spirit and scope of the invention. There is no intention to limit the invention to the specific form or forms disclosed, but on the contrary, the intention is to cover all modifications, alternative constructions, and equivalents falling within the spirit and scope of the invention, as defined by the claims. Thus, it is intended that the invention cover the modifications and variations of this invention provided they come within the scope of the appended claims and their equivalents.

We claim:

1. A method for providing changes in refractive power of an optical device, the method comprising:
   providing the optical device with an optical, polymeric lens material having an anterior surface and posterior surface and an optical axis intersecting the surfaces; and
   forming at least one laser-modified, gradient index (GRIN) layer disposed between the anterior surface and the posterior surface with continuous streams of light pulses from a visible or near-IR laser by continuously scanning the light pulses along regions of the optical, polymeric material at a varying scanning speed from 0.4 mm/s to 4 mm/s, varying average power of said laser, or both; wherein the at least one laser-modified GRIN layer comprises a plurality of adjacent refractive segments having a continuous change in the index of refraction in relation to the index of refraction of non-modified polymeric material, and the GRIN layer is characterized by a continuous variation in index of refraction of at least one of: (i) a portion of the plurality of adjacent refractive segments transverse to the direction scanned; and (ii) a portion of the plurality of refractive segments along the direction scanned; and wherein the at least one laser-modified, GRIN layer exhibits little or no scattering loss.

2. The method of claim 1, wherein the at least one laser-modified, GRIN layer disposed between the anterior surface and the posterior surface is arranged along a first axis oriented between about 45° to 135° to the optical axis.

3. The method of claim 1, wherein the polymeric lens material includes a photosensitizer.

4. The method of claim 3, wherein the photosensitizer comprises a chromophore having a two-photon, absorption cross-section of at least 10 GM between a laser wavelength range of 750 nm to 1100 nm.

5. The method of claim 4, wherein the photosensitizer is part of a polymerizable monomer or is physically dispersed within the optical polymer.

6. The method of claim 1, wherein scanning the light pulses along regions of the optical, polymeric material comprises a continuous stream of laser pulses having a pulse energy from 0.01 nJ to 20 nJ.

7. The method of claim 1, wherein the optical device is an intraocular lens or corneal inlay, and the forming of the at least one laser-modified GRIN layer is performed following the surgical placement of the optical device in an eye of a patient.

8. The method of claim 1, wherein the plurality of adjacent refractive segments have an independent line width of one to five μm and an intersegment spacing of two adjacent refractive segments is less than an average line width of the two adjacent segments.

9. The method of claim 1, wherein the plurality of adjacent refractive segments are essentially parallel segments.

10. The method of claim 2, wherein the plurality of adjacent refractive segments are concentric segments outwardly projected from a central point along the first axis.

11. The method of claim 1, wherein the plurality of adjacent refractive segments are arcuate or curved segments.

12. The method of claim 1, wherein the plurality of adjacent refractive segments of the GRIN layer are characterized by a constant positive change in the index of refraction of at least one of: (i) a portion of the plurality of refractive segments transverse to the direction scanned; and (ii) a portion of the plurality of refractive segments along the direction scanned.

13. The method of claim 1, wherein the plurality of adjacent refractive segments of the GRIN layer are characterized by a constant rate of increasing or decreasing positive change in the index of refraction of at least one of: (i) a portion of the plurality of refractive segments transverse to the direction scanned; and (ii) a portion of the plurality of refractive segments along the direction scanned.

14. The method of claim 1, wherein the at least one laser-modified, GRIN layer has a quadratic profile.

15. The method of claim 1 wherein the forming the at least one laser-modified, GRIN layer includes forming from two to ten laser-modified, GRIN layers.

16. The method of claim 2 wherein the forming the at least one laser-modified, GRIN layer includes forming from two to ten laser-modified, GRIN layers arranged either above or below the at least one laser-modified, GRIN layer along a second axis substantially perpendicular to the first axis.

17. The method of claim 16 wherein each GRIN layer has an independent thickness of from two μm to ten μm, and the plurality of GRIN layers exhibit little or no scattering loss.

18. The method of claim 16 wherein the two to ten GRIN layers has an interlayer spacing of non-modified polymeric lens material having a thickness of from five μm to 10 μm.

19. The method of claim 16, wherein the plurality of adjacent refractive segments of the at least one laser-modified, GRIN layer are characterized by a constant rate of increasing or decreasing positive change in the index of refraction of a portion of the plurality of refractive segments along the direction scanned.

20. The method of claim 1, wherein the plurality of adjacent refractive segments of the at least one laser-modified, GRIN layer are characterized by a constant rate of increasing or decreasing positive change in the index of refraction of a portion of the plurality of refractive segments along the direction scanned.

* * * * *